(12) United States Patent
Fairchild

(10) Patent No.: US 11,344,576 B2
(45) Date of Patent: May 31, 2022

(54) INDUCED PLURIPOTENT STEM CELLS PRODUCED FROM DENDRITIC CELLS

(71) Applicant: Oxford University Innovation Limited, Oxford (GB)

(72) Inventor: Paul J. Fairchild, Oxford (GB)

(73) Assignee: OXFORD UNIVERSITY INNOVATION LIMITED, Oxfordshire (GB)

( * ) Notice: Subject to any disclaimer, the term of this patent is extended or adjusted under 35 U.S.C. 154(b) by 525 days.

(21) Appl. No.: 16/071,414

(22) PCT Filed: Jan. 26, 2017

(86) PCT No.: PCT/GB2017/050201
§ 371 (c)(1),
(2) Date: Jul. 19, 2018

(87) PCT Pub. No.: WO2017/129981
PCT Pub. Date: Aug. 3, 2017

(65) Prior Publication Data
US 2019/0209610 A1 Jul. 11, 2019

(30) Foreign Application Priority Data
Jan. 27, 2016 (GB) .................................... 1601503

(51) Int. Cl.
| | | |
|---|---|---|
| *A61K 35/15* | (2015.01) | |
| *C12N 5/0784* | (2010.01) | |
| *C12N 5/074* | (2010.01) | |
| *A61P 31/00* | (2006.01) | |
| *A61P 35/00* | (2006.01) | |
| *C12N 5/0786* | (2010.01) | |
| *C12N 15/86* | (2006.01) | |
| *G01N 33/50* | (2006.01) | |

(52) U.S. Cl.
CPC .............. *A61K 35/15* (2013.01); *A61P 31/00* (2018.01); *A61P 35/00* (2018.01); *C12N 5/0639* (2013.01); *C12N 5/0645* (2013.01); *C12N 5/0696* (2013.01); *C12N 15/86* (2013.01); *G01N 33/505* (2013.01); *C12N 2501/22* (2013.01); *C12N 2501/2304* (2013.01); *C12N 2501/65* (2013.01); *C12N 2501/999* (2013.01); *C12N 2506/11* (2013.01); *C12N 2740/15011* (2013.01)

(58) Field of Classification Search
CPC ....... A61K 35/15; A61P 35/00; C12N 5/0645; C12N 15/86; C12N 5/0639; C12N 5/0696; C12N 2501/2304; C12N 2501/22; C12N 2506/11; C12N 2501/65; C12N 2501/999; C12N 2740/15011; G01N 33/505
See application file for complete search history.

(56) References Cited

U.S. PATENT DOCUMENTS

| | | | |
|---|---|---|---|
| 2009/0047263 A1 | 2/2009 | Yamanaka et al. | |
| 2010/0081199 A1 | 4/2010 | Slukvin et al. | |
| 2014/0050762 A1* | 2/2014 | Silk et al. ............ | C12N 5/0639 424/208.1 |

FOREIGN PATENT DOCUMENTS

| | | |
|---|---|---|
| EP | 2072618 A1 | 6/2009 |
| GB | 1601503.4 A1 | 1/2016 |
| WO | 2007/069666 A1 | 6/2007 |
| WO | 2010/033906 A2 | 3/2010 |
| WO | 2010/099539 A1 | 9/2010 |
| WO | 2012/115276 A1 | 8/2012 |
| WO | 2012/127206 A1 | 9/2012 |

OTHER PUBLICATIONS

McGovern et al., International Immunology, vol. 27, No. 2, pp. 65-72.*
Senju et al., "Immunotherapy with pluripotent stem cell-derived dendritic cells", Semin Immunopathol, 33:603-612, 2011.
Franco et al., 2008, Gen. Vacc. Ther. vol. 6: 1-11.
Mittag et al., 2011, J. Immunol. vol. 186: 6207-17.
Hoffmann et al., 2000, Can. Res. vol. 60: 3542-3549.
Hoene et al., 2006, J. Leuk. Biol. vol. 80: 1328-36.
Hoeffel et al., 2007, Immunity, vol. 27: 481-492.
Akira et al, Cell, 2006, 124, 783-801.
Avior et al, Hepatol, 2015, 62, 265-278.
Bachem et al, J. Exp. Med., 2010, 207, 1273-1281.
Bueno et al., Leukemia, 2016, 30, 674-682.
Carpenter et al, Blood, 2011, 117, 4008-4011.
Chhabra et al.: "Human Dendritic Cell-Derived Induced Pluripotent Stem Cell Lines Are Not Immunogenic", The Journal of Immunology, vol. 198, No. 5, Jan. 23, 2017 (Jan. 23, 2017), pp. 1875-1886.
Chhabra, Journal for ImmunoTherapy of Cancer, 2015, 3 (Suppl 2), 206.
Choe et al, Science, 2005, 309, 581-585.
Crozat et al, J. Exp. Med., 2010, 207, 1283-1292.
Engell-Noerregaard et al, Cancer Immunol. Immunother., 2009, 58, 1-14.

(Continued)

*Primary Examiner* — Thaian N. Ton
(74) *Attorney, Agent, or Firm* — Norton Rose Fulbright US LLP

(57) ABSTRACT

The invention relates to induced pluripotent stem cells (iPSCs) produced from source dendritic cells (DCs). The invention also relates to synthetic DCs re-differentiated the iPSCs and which display a definitive adult phenotype rather than a primitive fetal/neonatal phenotype. The invention also relates to methods for making and methods of using the iPSCs and DCs of the invention.

4 Claims, 12 Drawing Sheets

(56) References Cited

OTHER PUBLICATIONS

Feric & Radisic, Adv. Drug. Delivery Rev., 2016, 96, 110-134.
Gallois & Bhardwaj, Nature Med., 2010, 16, 854-856.
Goriely et al, J. Exp. Med., 2004, 199, 1011-1016.
Goriely et al, J. Immunol., 2001, 166, 2141-2146.
Hanna et al, Cell, 2010, 143, 508-825.
Hiromitsu et al.: "Antitumor immune response of dendritic cells (DCs) expressing tumor-associated antigens derived from induced pluripotent stem cells: in comparison to bone marrow-derived DCs.", International Journal of Cancer Jan. 15, 2014, vol. 134, No. 2, Jan. 15, 2014 (Jan. 15, 2014), pp. 332-341.
Kejin et al, Blood, 2011, vol. 117, No. 14, e109-e119.
Leishman et al, Current Opinion in Organ Transplantation, 2011, 16, 372-378.
Leishman et al.: "Differentiation of Dendritic Cells from Human Induced Pluripotent Stem Cells", Stem Cells and Cancer Stem Cells, vol. 12, Therapeutic Applications in Disease and Injury, Feb. 27, 2013 (Feb. 27, 2013), pp. 29-37, Springer, NL.
Lu et al, Blood, 2008, 112, 4475-4484.
Palucka et al, Immunity, 2010, 33, 464-478.
Poulin et al, J. Exp. Med., 2010, 207, 1261-1271.
Robson et al, Curr. Opin. Immunol., 2010, 22, 137-144.
Senju et al, Gene Therapy, 2011, vol. 18, 874-883.
Senju et al.: "Characterization of Dendritic Cells and Macrophages Generated by Directed Differentiation from Mouse Induced Pluripotent Stem Cells", Stem Cells, vol. 27, No. 5, May 1, 2009 (May 1, 2009), pp. 1021-1031.
Senju et al.: "Generation of dendritic cells and macrophages from human induced pluripotent stem cells aiming at cell therapy", Gene Therapy, vol. 18, No. 9, Mar. 24, 2011 (Mar. 24, 2011), pp. 874-883.
Silk et al.: "Cross-presentation of tumour antigens by human induced pluripotent stem cell-derived CD141+XCR1+dendritic cells", Gene Therapy, Nov. 10, 2011.
Stadtfeld & Hochedlinger, Genes Dev., 2010, 24, 2239-2263.
Tseng et al, Regen. Med., 2009, 4, 513-526.
Zhang et al.: "Generation and characterization of regulatory dendritic cells derived from murine induced pluripotent stem cells", Scientific Reports, vol. 4, Feb. 5, 2014.
Zhang et al.: "Generation of Mouse Pluripotent Stem Cell-Derived Proliferating Myeloid Cells as an Unlimited Source of Functional Antigen-Presenting Cells", Cancer Immunology Research, vol. 3, No. 6, Feb. 11, 2015 (Feb. 11, 2015), pp. 668-677.
Pulendran, "Modulating vaccine responses with dendritic cells and Toll-like receptors" Immunological Reviews, vol. 199, p. 227-250 (2004).
Schulz et al., "Toll-like receptor 3 promotes cross-priming to virus-infected cells" Letters to Nature, vol. 433, Feb. 24, 2005, p. 887-892.
Choi et al., "Generation of mature human myelomonocytic cells through expansion and differentiation of pluripotent stem cell-derived lin-CD34+CD43+CD45+ progenitors" J. Clin. Invest., 119(9): 2818-2829, 2009.
Dorner et al., "Selective Expression of the Chemokine Receptor XCR1 on Cross-presenting Dendritic Cells Determines Cooperation with CD8+ T Cells" Immunity, 31:823-833, 2009.
Edwards et al., "Toll-like receptor expresssion in murine DC subsets: lack of TLR7 expression by CD8a+ DC correlates with unresponsiveness to imidazoquinolines" Eur. J. Immunol, 33:827-833, 2003.
Fukuma et al., "Cancer prevention with semi-allogeneic ES cell-derived dendritic cells" Biochem. and Biophys. Research Comm., 335:5-13, 2005.
Fukushima et al., "Multiple Antigen-targeted Immunotherapy With a Galactosylceramide-loaded and Genetically Engineered Dendritic Cells Derived From Embryonic Stem Cells" J. Immunother., 32:219-231, 2009.
Hirata et al., "Prevention of Experimental Autoimmune Encephalomyelitis by Transfer of Embryonic Stem Cell-Derived Dendritic Cells Expressing Myelin Oligodendrocyte Glycoprotein Peptide along with TRAIL or Prgrammed Death-1 Ligand1" J. Immunology, 174:1888-1897, 2005.
Jarrossay et al., "Specialization and complementaity in microbial molecule recognition by human myeloid and plasmacytoid dendritic cells" Eur. J. Immunol., 31:3388-3393, 2001.
Jongbloed et al., "Human CD141+ (BDCA-3)+ dendritic cells (DCs) represent a unique myeloid DC subset that cross-presents necrotic cell antigens" JEM, 207(6):1247-1260, 2010.
Lin et al., "Development of Feeder-Free Culture Systems for Generation of ckit+sca1+ Progenitors from Mouse iPS Cells" Stem Cell Rev., 7(3):736-747, 2011.
Muzio et al., "Differential Expresssion and Regulation of Toll-Like Receptors (TLR) in Human Leukocytes: Selective Expression of TLR3 in Dendritic Cells" J. Immunology. 164:5998-6004, 2000.
Senju et al., "Pluripotent stem cell-derived dendritic cells for immunotherapy" Frontiers in Bioscience, E2:1520-1527, 2010.
Senju et al., "Pluriptent stem cells as source od dendritic cells for immune therapy" Int. J. Hematol, 91:392-400, 2010.
Su et al., "Differentiation of Human Embryonic Stem Cells into Immunostimulatory Dendritic Cells under Feeder-Free Culture Conditions" Clin. Cancer Res. 14(19):6207-6217, 2008.
Kadowaki, Norimitsu, et al.: Subsets of Human Dendritic Cell Precursors Express Different Toll-like Receptors and Respond to Different Microbioal Antigens; (2001) J. Exp. Med. 863-869.
Bauer, Marc, et al.: Bacterial CpG-DNA Triggers Activation and Maturation of Human CD11c−, CD123+ Dendritic Cells; (2001) J. Immunol. 166: P5000-5007.
Krug, Anne et al.: Toll-like Receptor Expression Reveals CpG DNA as a Unique Microbial Stimulus for Plasmacytoid Dendritic Cells which synergizes with CD40 Ligand to Induce High Amounts of IL-12; (2001) Eur. J. Immunol. 31; 3026-3037.
Hartmann, G. et al.: CpG DNA: A Potent Signal for Growth, Activation, and Maturation of Human Dentritic Cells; (1999); PNSA 96: P9305-9310.
Feuerstein et al.: "A method for the production of cryopreserved aliquots of antigen-preloaded, mature dendritic cells ready for clinical use", Journal of Immunological Methods, vol. 245, No. 1-2, Nov. 1, 2000 (Nov. 1, 2000), pp. 15-29, Elsevier Science Publishers B.V., Amsterdam, NL.

\* cited by examiner

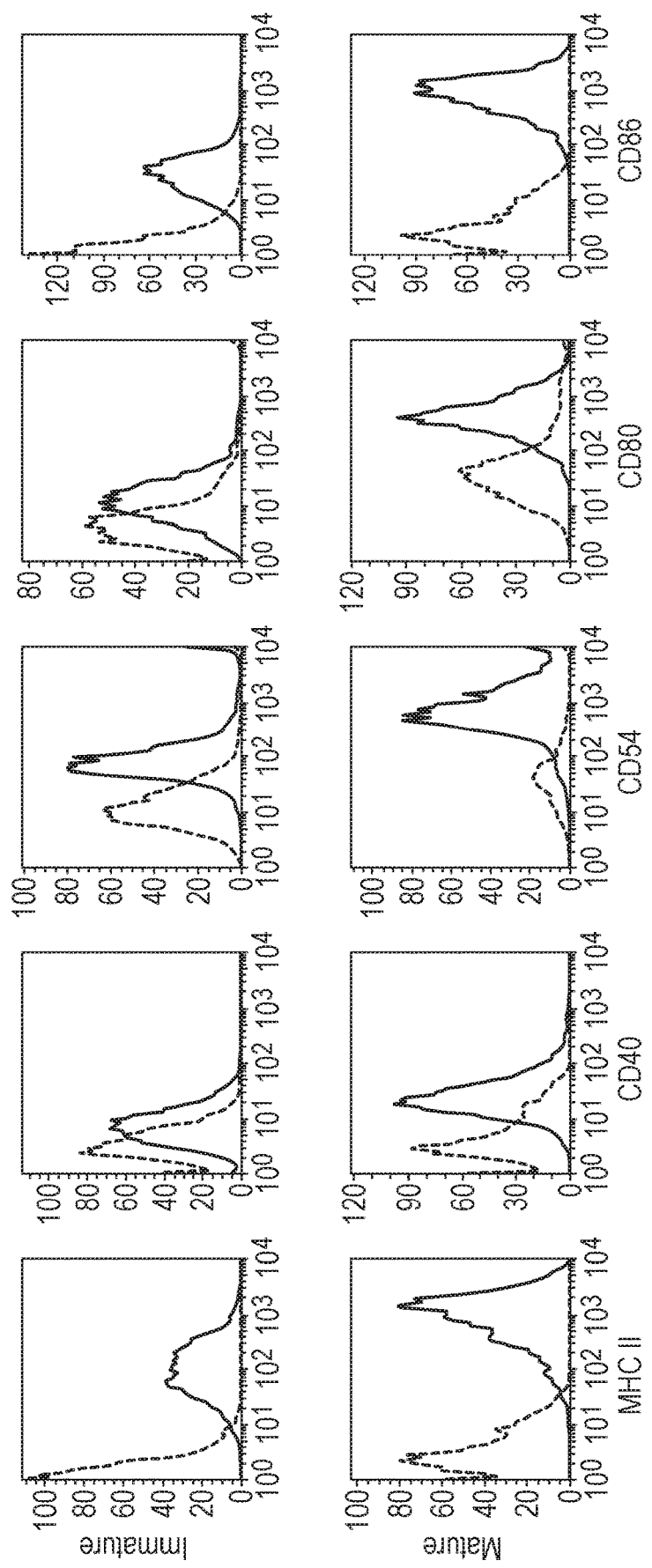

INDUCED PLURIPOTENT STEM CELLS PRODUCED FROM DENDRITIC CELLS

CROSS REFERENCE TO RELATED APPLICATIONS

This application is a national phase application under 35 U.S.C. § 371 that claims priority to International Application No. PCT/GB2017/050201 filed Jan. 26, 2017, which claims priority to United Kingdom Patent Application No. 1601503.4 filed on Jan. 27, 2016, all of which are incorporated herein by reference in their entirety.

FIELD OF THE INVENTION

The invention relates to induced pluripotent stem cells (iPSCs) produced from source dendritic cells (DCs). The invention also relates to synthetic DCs re-differentiated the iPSCs and which display an adult phenotype rather than a fetal/neonatal phenotype. The invention also relates to methods for making and methods of using the iPSCs and DCs of the invention.

BACKGROUND TO THE INVENTION

The use of dendritic cells (DCs) to prime responses to tumor-associated antigens (TAAs) provides a promising approach to cancer immunotherapy (Palucka et al., *Immunity* 33, 464-478 (2010)), but clinically-relevant responses have frequently been disappointing (Engell-Noerregaard et al., *Cancer Immunol. Immunother.* 58, 1-14 (2009); and Robson et al., *Curr. Opin. Immunol.* 22, 137-144 (2010)). This is partly due to the properties of the DCs most commonly used. Currently, autologous DC, differentiated in vitro from the patient's own peripheral blood monocytes, remain the preferred source of cells for cancer immunotherapy. These monocyte-derived DCs (moDCs) show significant donor-to-donor variation, which is frequently compounded by the side-effects of chemotherapy. Furthermore, moDCs display a limited capacity for cross-priming of antigen specific $CD8^+$ cytotoxic T lymphocytes (CTLs), creating a dependence on the use of exogenous peptides derived from TAAs and further restricting the scope of such an approach to those HLA haplotypes for which the immunodominant epitopes are known. Since $CD8\alpha^+$ DC in mice are peculiarly capable of cross-presentation, the recent identification of $CD141^+$ $XCR1^+$ DC as their functional equivalent in humans (Bachem et al., *J. Exp. Med.* 207, 1273-1281 (2010); and Crozat et al., *J. Exp. Med.* 207, 1283-1292 (2010)) has suggested that this subset may be better suited to the induction of anti-tumor responses (Gallois & Bhardwaj, *Nature Med.* 16, 854-856 (2010)). However, such cells are only present in trace numbers in peripheral blood and low yields are obtained following the culture of progenitors from cord blood (Poulin et al., *J. Exp. Med.* 207, 1261-1271 (2010)). As a result, they do not represent a feasible treatment for cancer.

One way of obtaining sufficient numbers of suitable DCs is to produce them from induced pluripotent stem cells (iPSCs) or embryonic stem cells (ESCs). However, cell types, such as cardiomyocytes, neurons, hepatocytes and erythrocytes, differentiated from ESCs and iPSCs display a primitive 'fetal' or 'neonatal' phenotype which may limit their therapeutic utility (Feric & Radisic, *Adv. Drug Delivery Rev.* 96, 110-134 (2016); and Avior et al., *Hepatol.* 62, 265-278 (2015)). In the case of erythrocytes, cells fail to enucleate and rarely progress beyond the expression of fetal haemoglobin to the adult isoform which prevents their use in transfusion medicine (Lu et al. *Blood* 112, 4475-4484 (2008)). DCs derived from iPSCs and ESCs display a similar fetal phenotype characterised by low expression of MHC class II and co-stimulatory molecules. Furthermore, iPSC-derived DC (ipDC) have very limited ability to secrete IL-12 required for Th1 polarisation and activation of cytotoxic T cells (CTL), thereby limiting their immunogenicity and rendering them more tolerogenic. This phenotype has been reported among human neonatal DC and is due to active repression of the p35 subunit of IL-12 (Goriely S, Vincart B, Stordeur P et al. *J. Immunol.* 166, 2141-2146 (2001); and Goriely S, Van Lint C, Dadkhah R et al.: A defect in nucleosome remodelling prevents IL-12(p35) gene transcription in neonatal dendritic cells. *J. Exp. Med.* 199, 1011-1016 (2004)).

SUMMARY OF THE INVENTION

The inventors have surprisingly demonstrated that it is feasible to exploit the epigenetic memory that iPSC display for the cell types from which they were derived, in order to overcome this block in differentiation. In particular, the inventors have surprisingly demonstrated that, by reprogramming terminally differentiated DC to pluripotency, DC re-differentiated from them may display many of the features of the source population unlike DC differentiated from ESC or iPSC derived from conventional dermal fibroblasts or any other somatic cell type.

Unexpectedly, the inventors found terminally differentiated DC to be tractable candidates for reprogramming to iPSC readily forming colonies after transduction and with high efficiency. Furthermore, DC re-differentiated from them expressed constitutively high MHC class II, CD40, CD80 and CD86 and secreted copious IL-12, unlike control ipDC from fibroblast-derived iPSC. Furthermore, this novel form of DCs performs favourably on a per cell basis compared with conventional DC in standard assays of immunogenicity such as the allogeneic mixed leukocyte reaction. Deriving iPSCs from DCs as a starting population therefore overcomes all issues associated with the fetal/neonatal phenotype.

These findings are unexpected because DCs are highly adapted to sensing the presence of viral pathogens and respond vigorously to heterologous nucleic acids. It was anticipated, therefore, that attempts to transduce them with reprogramming factors would merely lead to their rapid maturation followed by cell death 2-3 days later, thereby preventing reprogramming to pluripotency. That was not the case. Although epigenetic memory is thought to be lost from iPSCs after approximately 10 passages in vitro, the inventors have found that, unexpectedly, the passage of the iPSCs does not adversely affect the phenotype of the DC which remain highly immunogenic beyond passage 10, reverting to a more fetal phenotype around P15.

This approach has significant clinical implications since moDCs are easily cultured from the peripheral blood of patients and could be used as the starting material for the production of an iPSC line rather than a skin punch biopsy. Results suggest that the choice of starting material will influence the end use of the ipDC: whereas dermal fibroblasts may still be the starting material of choice for DC aimed at the induction of antigen-specific tolerance, mo DC are likely to be a more logical starting point for vaccination purposes.

The invention therefore provides an induced pluripotent stem cell (iPSC) produced from a source dendritic cell (DC).

As discussed in more detail below, the source DC may be modified to render it more tolerogenic before it is used to produce the iPSC of the invention.

The invention also provides:
- a population comprising two or more iPSCs of the invention;
- a population comprising more than $5.0 \times 10^5$ iPSCs of the invention;
- a method of producing a population of iPSCs of the invention, comprising culturing source DCs under conditions which reprogram the source DCs to produce the iPSCs;
- a synthetic DC re-differentiated from an iPSC produced from a source DC, wherein the synthetic DC displays a definitive adult phenotype rather than a primitive fetal/neonatal phenotype;
- a population comprising two or more synthetic DCs of the invention;
- a population comprising more than $5.0 \times 10^5$ synthetic DCs of the invention;
- a pharmaceutical composition comprising (a) a synthetic DC of the invention or a population of synthetic DCs of the invention and (b) a pharmaceutically acceptable carrier or diluent;
- a method of producing a population of synthetic DCs of the invention, comprising culturing iPSCs of the invention under conditions which induce the iPSCs to differentiate into DCs;
- a method of producing a population of synthetic DCs of the invention, comprising (a) carrying out a method of the invention and (b) culturing the iPSCs produced in step (a) under conditions which induce the iPSCs to differentiate into DCs;
- a method of inducing a T cell response to an antigen in a patient in need thereof, comprising administering to the patient an immunologically effective number of synthetic DCs of the invention which are loaded or transfected with the antigen and thereby inducing a T cell response to the antigen in the patient; and
- a method of inducing tolerance to an antigen in a patient in need thereof, comprising administering to the patient an immunologically effective number of the tolerogenic DCs of the invention and thereby inducing tolerance to the antigen in the patient, wherein the tolerogenic DCs are loaded or transfected with the antigen.

DETAILED DESCRIPTION OF THE INVENTION

Figure 1A:
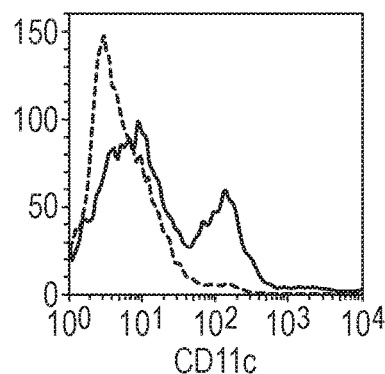
FIG. 1: Characterisation of source DCs. Mouse bone marrow progenitors cultured in GM-CSF for 7 days yield a mixed population of cells, a proportion of which express the DC restricted marker CD11c (A). When purified using CD11c-magnetic beads, the resulting bone marrow-derived DCs (bmDC) show a pronounced dendritic morphology (B), express MHC class II, CD40 and CD54 in addition to CD11c (C), and stimulate primary T cell responses in the allogeneic mixed leukocyte reaction (D).
Figure 1B:
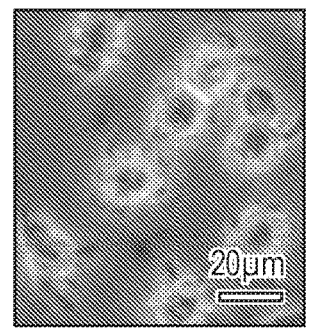
Figure 1C:
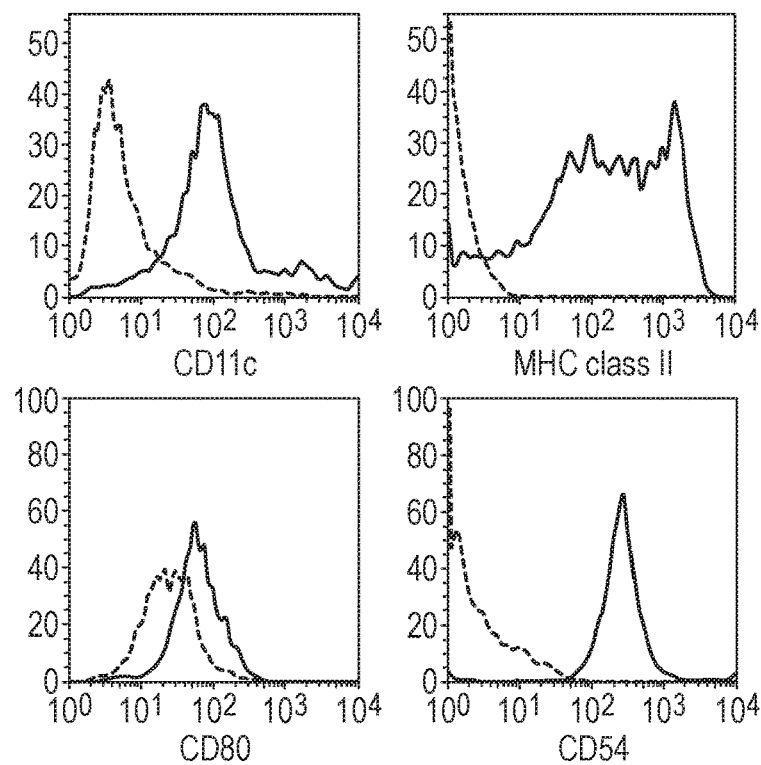
Figure 1D:
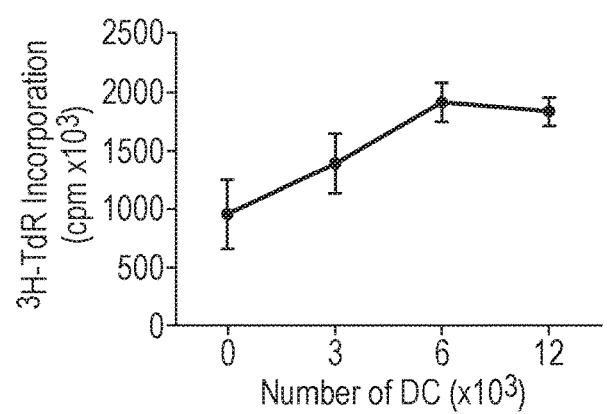

It is to be understood that different applications of the disclosed methods may be tailored to the specific needs in the art. It is also to be understood that the terminology used herein is for the purpose of describing particular embodiments of the invention only, and is not intended to be limiting.

In addition, as used in this specification and the appended claims, the singular forms "a", "an", and "the" include plural referents unless the content clearly dictates otherwise. Thus, for example, reference to "a cell" includes "cells", reference to "an antigen" includes two or more such antigens, reference to "a patient" includes two or more such patients, and the like.

All publications, patents and patent applications cited herein, whether supra or infra, are hereby incorporated by reference in their entirety.

Source DCs

Any source DC may be used in the invention. The source DC can be identified as a dendritic cell using standard methods known in the art, including morphology, expression of lineage restricted markers, structural and functional characteristics. These are discussed in more detail below with reference to the synthetic DCs of the invention.

The source DC may be terminally differentiated. The source DC is a preferably a conventional myeloid DC, a plasmacytoid DC, an epidermal Langerhans cell or a dermal DC. The conventional DC is a $CD1c^+$ conventional DC or a $CD141^+$ conventional DC. The plasmacytoid DC is preferably a $CD303^+$ plasmacytoid DC. The skilled person will appreciate how to obtain these cells.

The source DC is preferably differentiated from a circulating precursor isolated from peripheral blood. The circulating precursor is preferably a monocyte. Monocytes may be differentiated in vitro into a conventional DC, for example, upon culture for 6-8 days in 50 ng/ml GM-CSF and 100 ng/ml of IL-4.

The source DC was preferably modified before it was used to form the iPSC to increase its immunogenicity. For instance, the source DC was preferably modified by exposure to inflammatory stimuli with or without appropriate ligands for pattern recognition receptors. The use of an immunogenic source DC allows the production of an immunogenic synthetic DC in accordance with the invention.

The source DC was preferably modified before it was used to form the iPSC to favour a tolerogenic phenotype. Source DCs may be treated with a variety of pharmacological agents to render them more tolerogenic. These agents include, but are not limited to, Vitamin D3, dexamethasone, Interleukin-10, Rapamycin and Transforming-Growth Factor-β (Leishman et al., *Current Opinion in Organ Transplantation* 2011, 16, 372-378). These modulate the expression of co-stimulatory molecules, cytokines and inhibitory receptors which impacts the outcome of antigen-presentation to T cells. Since the expression of these key molecules may be controlled at the epigenetic level, there is value in using a source DC that has been modulated in this way in order to generate a synthetic DC that has 'captured' the epigenetic profile that defines a tolerogenic phenotype. This approach enables the direct differentiation from an appropriate iPSC line of DCs that are already fully predisposed to the induction of tolerance.

The invention also encompasses gene editing of the source DC, for instance using the CRISPR/Cas9 system, to knock out genes, such as CD40, thereby reinforcing a tolerogenic phenotype.

The source DC is typically human. However, the source DC may be derived from another mammalian animal, such as a commercially farmed animal, such as a horse, a cow, a sheep, a fish, a chicken or a pig, a laboratory animal, such as a mouse or a rat, or a pet, such as a guinea pig, a hamster, a rabbit, a cat or a dog.

iPSCs of the Invention

The iPSCs of the invention typically display the characteristic morphology of human embryonic stem cells (hESCs), express the pluripotency-associated markers SSEA-4 and TRA1-60, the transcription factors Oct-4 and Nanog and differentiate in vitro into cell types derived from each of the three embryonic germ layers.

Techniques for producing and culturing iPSCs are well known to a person skilled in the art. Suitable conditions are discussed below.

An iPSC of the invention may be isolated, substantially isolated, purified or substantially purified. The iPSC is isolated or purified if it is completely free of any other components, such as culture medium, other cells of the invention or other cell types. The iPSC is substantially isolated if it is mixed with carriers or diluents, such as culture medium, which will not interfere with its intended use. Alternatively, the iPSC of the invention may be present in a growth matrix or immobilized on a surface as discussed below.

Method of Producing an iPSC of the Invention

The invention also provides a method of producing a population of iPSCs of the invention, comprising culturing source DCs under conditions which reprogram the source DCs to produce the iPSCs. Any of the source DCs discussed above may be used.

The method preferably comprises culturing the source DCs with a Sendai virus system, a retroviral system, a lentiviral system, microRNA or other reprogramming factors which is/are capable of reprogramming the source DCs to produce the iPSCs.

Induced pluripotent stem cells and methods of producing them are known in the art. A method for inducing pluripotency of differentiated cells, such as somatic cells, was first disclosed by Yamanaka (WO 2007/069666). In this method, somatic cells are reprogrammed using three main nuclear reprogramming factors, namely an Oct family gene, a Klf family gene and a Sox family gene (preferably Sox2). The factors are preferably Oct3/4, Klf4 and Sox2. A fourth reprogramming factor, namely the product of a Myc family gene (preferably c-Myc), may also be used. Numerous different methods have since been disclosed for inducing pluripotency in somatic cells. Such methods are reviewed in Hanna et al., *Cell* 2010 143, 508-25; and Stadtfeld & Hochedlinger, *Genes Dev.* 2010 24, 2239-63. One method is described in Carpenter, L. et al. *Blood* 117, 4008-4011 (2011).

An important method for reprogramming is the use of messenger RNA specific for the reprogramming factors since this does not involve any genetic modification of the cells and the risk of tumorigenesis. Another method is to produce from the reprogramming genes, recombinant proteins modified to permit their penetration of the plasma and nuclear membranes. Other reprogramming factors include, but are not limited to, small compounds synthesized through medicinal chemistry.

The method preferably further comprises isolating clonal lines of iPSCs of the invention. For instance, the method preferably further comprises isolating clonal lines of iPSCs of the invention by limiting dilution or the manual 'picking' of individual colonies.

Synthetic DCs of the Invention

The invention also provides a synthetic DC re-differentiated from an induced pluripotent stem cell (iPSC) produced from a source DC, wherein the synthetic DC displays a definitive adult phenotype rather than a primitive fetal/neonatal phenotype. The synthetic DCs of the invention have numerous advantages. The key advantages will be summarized here. However, further advantages will become apparent from the discussion below.

The synthetic DCs advantageously display an adult phenotype rather than a fetal/neonatal phenotype. This means that they retain most, if not all, of the features of the source DCs from which they were ultimately derived. The synthetic DCs preferably advantageously display an adult phenotype that is comparable to the source DC from which they were derived. This is discussed in more detail below. The synthetic DCs of the invention can then be used therapeutically in any way in which the source DCs may be used.

As discussed in more detail above, the human iPSCs are produced from source DCs, which may be taken from a human individual. Since the synthetic DCs are produced from these iPSCs, they may be autologous for the patient to be treated and thereby avoid the risk of immunological rejection by the patient.

It is possible, in principle, to produce an unlimited number of iPSCs from a single individual, since iPSC are capable of indefinite self-renewal. It is certainly possible to produce very large numbers of iPSCs from a single individual. The synthetic DCs of the invention can therefore be made in large numbers. It is advantageously possible to provide many more synthetic DCs using the invention than by isolating the relevant cells from the peripheral blood of a patient. It is also advantageously possible to provide large numbers of synthetic DCs belonging to subsets that are not normally accessible since they are restricted to specific anatomical locations rather than circulating in the peripheral blood. This is explained in more detail below.

iPSCs can be maintained in culture indefinitely or used to produce a renewable bank from which synthetic DCs of the invention can be produced. Numerous populations of the synthetic DCs of the invention can be made from one population of iPSCs. This facilitates repeated treatment of the patient without the need to take numerous samples, such as peripheral blood. Likewise, numerous subsets of synthetic DCs can be produced from one population of iPSCs enabling the cells of the invention to be tailored to the therapeutic needs of the patient.

The synthetic DCs of the invention are produced in clinically relevant conditions, for instance in the absence of trace amounts of endotoxins and other environmental contaminants, as well as animal products such as fetal calf serum. This makes the synthetic DCs of the invention particularly suitable for administration to patients.

Since the synthetic DCs of the invention are produced from iPSCs, they are substantially homologous and may be autologous. They also avoid donor-to-donor variation, which frequently occurs with moDCs. Numerous populations of synthetic DCs of the invention can be produced from a single sample take from the patient before any other cancer therapy, such as chemotherapy or radiotherapy, has begun. Therefore, the synthetic DCs of the invention can avoid any of the detrimental effects of those treatments.

The synthetic DCs of the invention can also be made more quickly than DCs from other populations of pluripotent cells, such as human embryonic stem cells (hESCs). DCs can be produced from iPSCs in less than 30 days, rather than the 30 to 40 days it takes to produce DCs from hESCs.

The production of synthetic DCs from iPSCs avoids the moral and ethical implications involved with using other types of stem cells, such human embryonic stem cells (hESCs).

As discussed in more detail below, the synthetic DCs of the invention may be surprisingly responsive to ligands of various Toll-like receptors (TLRs), especially TLR2, TLR3, TLR4, TLR7 and TLR9, and so their ability to cross present antigens in vivo may be fine-tuned depending on which subset of synthetic DCs is produced.

Synthetic CD141$^+$ DCs of the invention may advantageously be used to induce CTL responses to a particular antigen in a human patient. The synthetic DCs may, therefore, be used for the effective treatment of a variety of diseases in which CTL responses are preferred, such as cancer or chronic infections by a pathogen.

DCs have different stages in their development during which they, for example, predominately take up antigen, rather than present it. For example, it is thought that DCs may have immature stages characterised by the uptake of large amounts of potential antigens and more mature stages characterised by lower amounts of antigen uptake, but increased capacity for presentation of the antigens they acquired previously. The synthetic DCs of the invention may initially be immature but may be induced to mature as evidenced by their increased ability to present antigen to mature CD4$^+$ T cells and, if directed in their differentiation into the CD141$^+$ subset, increased ability to cross present antigen to naïve or memory CD8$^+$ T cells. Methods for making mature DCs are disclosed in more detail below. The synthetic DCs may of course be manipulated in vitro and this may allow control of whether the cells are exposed to stimuli which promote DC maturation. Thus, by ensuring that the cells are exposed to stimuli responsible for inducing maturation, the resultant cells may be used to promote an immune response when they are transferred to a patient.

The synthetic DCs of the invention can be identified as dendritic cells using standard methods known in the art, including morphology, expression of lineage restricted markers, structural and functional characteristics. The synthetic DCs will express detectable levels of cell surface markers known to be characteristic of dendritic cells. In particular the synthetic DCs may express detectable levels of any one of CD11c, CD209 (also known as DC-SIGN), CD13, low levels of CD200R, CD11b, CD83 and CD40. The cells may be CD14$^{lo}$. In some cases the cells may express all of CD11c, CD209 and CD13 and may also be CD14$^{lo}$.

The synthetic DCs of the invention typically express MHC molecules. The DCs of the invention typically express both MHC class I and MHC class II. The synthetic DCs of the invention preferably express detectable levels of MHC class II. Any of the HLA haplotypes may be present on the synthetic DCs of the invention, as defined by the donor from whom they are derived.

In response to a maturation cocktail, such an one comprising tumor necrosis factor-α (TNFα), prostaglandin-E$_2$ (PGE$_2$), interleukin-1β (IL-1β) and interferon-γ (IFNγ), the synthetic DCs of the invention will secrete high concentrations of the pro-inflammatory cytokine IL-6.

Morphologically, DCs are typically characterised by extensive veils of cytoplasm and individual cells with many dendrites. Other defining characteristics of DCs are their ability to phagocytose particulate material and endocytose soluble protein antigens while immature and their ability to activate naïve T cells upon maturation, as exemplified by the allogeneic mixed leukocyte reaction (MLR). In an MLR, DCs are cultured together with naïve allogeneic lymphocytes. Due to the histocompatibility mismatch between the cells, T cells recognise allogeneic MHC molecules expressed by DC as foreign and respond by proliferating vigorously in culture.

The synthetic DC may be any of the types of DC discussed above with reference to the source DC. The synthetic DC may be the same type of DC as the source DC from which it is ultimately derived. Alternatively, the synthetic DC may be a different type from the source DC from which is ultimately derived.

In essence, there are two sets of characteristics that define a DC. The first are features common to all subsets of DC, the second are subset specific. All DCs will, for instance, express certain molecules, such as MHC class II and co-stimulatory molecules, secrete IL-12 and have the capacity to acquire, process and present protein antigens to naïve T cells. However, other features are specific to individual subsets. For example, CD141+ DCs are especially adapted to cross-presentation. CD303+ plasmacytoid DCs secrete copious quantities of type I interferons (IFN).

By using source DCs as the material from which the iPSCs are derived, the invention is capturing, at the epigenetic level, the 'essence of a DC', i.e. those features common to all DCs, rather than subset-restricted characteristics. However, once such an iPSC is produced, its pluripotency means that, in theory, it can be differentiated it into any subset of DC, each of which would be enhanced in its functional capacity by recalling the epigenetic memory of the source DC to optimise those characteristics common to all DCs.

In other words, the invention could start with a moDC as source material and, via an iPSC intermediate, generate a plasmacytoid DC. Alternatively, the invention could start with a Langerhans cells and by inducing pluripotency, could generate a CD141+ cross-presenting DC. The key issue is, however, that whatever subsets of DCs are differentiated, they are likely to display a definitive adult phenotype comparable to the equivalent subset in vivo rather than exhibiting the block in differentiation associated with the fetal phenotype. The Table below shows examples of preferred combinations of subsets of source and synthetic DCs (i.e. the synthetic DC in a particular row is preferably produced from the source DC in the same row).

| Source DC | Synthetic DC |
| --- | --- |
| moDC | Plasmacytoid DC |
| moDC | CD141+ cross-presenting DC |
| Plasmacytoid DC | Plasmacytoid DC |
| Langerhans cell | CD141+ cross-presenting DC |

Adult Phenotype

The synthetic DC of the invention displays a definitive adult phenotype rather than a primitive fetal/neonatal phenotype. The synthetic DC displays one or more features of, preferably all of, the features of the source DC from which it was derived. The synthetic DC of the invention preferably displays an identical adult phenotype to the source DC from which it was derived. The synthetic DC of the invention may display an identical adult phenotype to a different type of source DC from the source DC from which it was derived. Preferred combinations of different types of source and synthetic DCs are shown in the Table above. The phenotype of the synthetic and source DCs may be measured using any technique discussed herein.

The synthetic DC preferably displays a definitive adult phenotype rather than a primitive fetal/neonatal phenotype because it expresses detectable levels of (i) MHC class II, (ii) CD40, (iii) CD54, (iv) CD80, (v) CD86 or (vi) any combination of (i) to (v). The combination (vi) may be {i}; {ii}; {iii}; {iv}; {v}; {i,ii}; {i,iii}; {i,iv}; {i,v}; {ii,iii}; {ii,iv}; {ii,v}; {iii,iv}; {iii,v}; {iv,v}; {i,ii,iii}; {i,ii,iv}; {i,ii,v}; {i,iii,v}; {i,iv,v}; {ii,iii,iv}; {ii,iii,v}; {ii,iv,v}; {iii,iv,v}; {i,ii,iii,iv}; {i,ii,iii,v}; {i,ii,iv,v}; {i,iii,iv,v}; {ii,iii,iv,v} or {i,ii,iii,iv,v} (where the commas=and). The combination is most preferably all of (i) to (v).

The synthetic DC preferably displays an adult phenotype rather than a fetal/neonatal phenotype because it expresses a level of any one of (i) to (vi) which is comparable to or greater than the source DC. The synthetic DC preferably expresses a level of any one of (i) to (vi) which is comparable to the source DC when it expresses a level of any one of (i) to (vi) which is at least 70%, at least 75%, at least 80%, at least 85%, at least 90%, at least 95%, at least 97%, at least 98%, at least 99% or 100% of the level of expression of any of (i) to (vi) by the source DC.

The synthetic DC preferably displays a definitive adult phenotype rather than a primitive fetal/neonatal phenotype because it expresses a greater level of any one of (i) to (vi) than a DC displaying a fetal/neonatal phenotype and differentiated from an iPSC derived from a somatic cell, such as a conventional dermal fibroblast. The synthetic DC preferably expresses a greater level of any one of (i) to (vi) than the DC displaying a fetal/neonatal phenotype when it expresses a level of any one of (i) to (vi) which is at least 120%, at least 150%, at least two fold, at least three fold, at least four fold, at least five fold, at least 10 fold, at least 100 fold or at least 1000 fold the level of expression of any of (i) to (vi) by the DC displaying a fetal/neonatal phenotype.

The synthetic DC preferably displays a definitive adult phenotype rather than a primitive fetal/neonatal phenotype because it secretes interleukin 12 (IL-12). The synthetic DC preferably displays a definitive adult phenotype rather than a primitive fetal/neonatal phenotype because it secretes a level of interleukin 12 (IL-12) which is comparable to or greater than the source DC. The synthetic DC preferably secretes a level of interleukin 12 (IL-12) which is comparable to the source DC if it secretes a level of IL-12 which is at least 50%, at least 75%, at least 80%, at least 85%, at least 90%, at least 95%, at least 97%, at least 98%, at least 99% or 100% of the level of secretion of IL-12 by the source DC.

The synthetic DC preferably displays a definitive adult phenotype rather than a primitive fetal/neonatal phenotype because it secretes a greater level of IL-12 than a DC displaying a fetal/neonatal phenotype and differentiated from a iPSC derived from a somatic cell, such as a conventional dermal fibroblast. The synthetic DC preferably secretes a greater level of IL-12 than the DC displaying a fetal/neonatal phenotype when it secretes a level of IL-12 which is at least two fold, at least three fold, at least four fold, at least five fold, at least 10 fold, at least 100 fold or at least 1000 fold the level of secretion of IL-12 by the DC displaying a fetal/neonatal phenotype.

The synthetic DC preferably displays a definitive adult phenotype because it performs at a comparable level to the source DC in a standard assay of immunogenicity. The comparable level is preferably at least 70%, at least 80%, at least 90%, at least 95%, at least 97%, at least 98%, at least 99% or 100% of the level of the source DC. The synthetic DC preferably displays an adult phenotype because it performs as well as or better than the source DC in a standard assay of immunogenicity. The assay is preferably an allogeneic mixed leukocyte reaction or another assay capable of tracking the activation of antigen-specific T cells.

Standard methods known in the art may be used to determine the detectable expression and level of expression of the various markers discussed above. Suitable methods include, but are not limited to, immunocytochemistry, flow cytometry, western blotting and quantitative PCR. DC responses to antigens may also be measured using standard assays known in the art. Suitable methods include, but are not limited to, enzyme-linked immunosorbent assays (ELISA) and ELISpot for the secretion of cytokines, enhanced mixed leukocyte reactions and up-regulation of co-stimulatory molecules and maturation markers, measured by flow cytometry. Specific methods that may be used are disclosed in the Example.

Synthetic Plasmacytoid DCs

The synthetic DC of the invention may be a plasmacytoid DC as discussed above. These are typically derived with high efficiency from plasmacytoid source DCs, but could also be differentiated with lower efficiency from iPSC derived from other source material. The synthetic DC of the invention preferably expresses detectable levels of the plasmacytoid DC markers CD123 and CD303. The synthetic DC preferably expresses detectable levels of Toll like receptor 3 (TLR3) and/or responds to viral challenge by secretion of type I interferons.

Synthetic Cross-Presenting DCs on the Invention

The synthetic DC is preferably capable of cross presenting an antigen to naïve $CD8^+$ T lymphocytes. The synthetic DC of the invention preferably expresses detectable levels of CD141. This cell surface antigen is typically expressed by cells capable of antigen cross presentation.

The synthetic DC of the invention preferably either expresses detectable levels of certain TLRs or responds to ligands of particular TLRs. TLRs are pattern recognition receptors that bind to moieties that are conserved amongst microbes known as pathogen associated molecular patterns (PAMPs). Binding of TLR ligands to TLRs initiates signalling cascades inside DCs that result in the production of pro-inflammatory cytokines and up-regulation of co-stimulatory molecules important in initiating immune responses. The ability of the synthetic DCs of the invention to respond to various TLR ligands is advantageous because it allows the ability of the synthetic DCs to cross present antigen to naïve $CD8^+$ T cells in vivo to be improved by ligands of TLRs.

DC responses to TLR ligands may also be measured using standard assays known in the art. Suitable methods include, but are not limited to, enzyme-linked immunosorbent assays (ELISA) and ELISpot for the secretion of cytokines, enhanced mixed leukocyte reactions and up-regulation of co-stimulatory molecules and maturation markers, measured by flow cytometry. Specific methods that may be used are disclosed in the Example.

The synthetic DC of the invention preferably expresses detectable levels of TLR9. TLR9 recognizes unmethylated 2'-deoxyribo(cytidine-phospho-guanosine) (CpG) DNA motifs that are frequently present in bacteria and viruses, but are rare in mammalian cells. Since the DCs of the invention express TLR9, they are capable of recognising CpG DNA motifs. The DCs of the invention may be used to treat chronic bacterial or viral infections. The therapeutic methods of the invention may also involve combined therapy with DCs of the invention and one or more CpG motifs. $CD141^+XCR1^+$ DCs isolated from human peripheral blood do not express detectable levels of TLR9 (Bachem et al., *J. Exp. Med.* 207, 1273-1281 (2010); and Crozat et al. *J. Exp. Med.* 207, 1283-1292 (2010)).

The synthetic DC of the invention preferably expresses detectable levels of TLR3. TLR3 was originally identified as recognizing a synthetic analog of double-stranded RNA (dsRNA), namely polyinosinic-polycytidylic acid (poly(I:C)), which mimics viral infection and induces antiviral immune responses by promoting the production of both type I interferon and inflammatory cytokines (Choe et al., *Science* 309, 581-585 (2005)). The synthetic DCs of the invention may be used to treat chronic viral infections. The therapeutic methods of the invention may involve combined therapy with synthetic DCs of the invention and one or more TLR3 agonists, such as poly(I:C)s.

The synthetic DC of the invention preferably expresses detectable levels of TLR7. TLR7 recognises RNA viruses in a replication-independent manner.

The synthetic DC of invention preferably expresses low levels of TLR2 and TLR4 when determined by flow cytometry. In any case, the synthetic DCs of the invention preferably respond to ligands of TLR2 and TLR4 in functional assays, such as the secretion of IL-6, detected by ELISA assays. TLR-2 (also known as CD282) is a surface membrane receptor protein which plays a fundamental role in pathogen recognition and activation of innate immunity. This protein is expressed most abundantly in peripheral blood leukocytes, and mediates host response to Gram-positive bacteria and yeast via stimulation of NF-κB. TLR2 is involved in the recognition of a wide range of PAMPs derived from bacteria, fungi, parasites and viruses (Akira, et al., *Cell* 124, 783-801 (2006)). These include lipopeptides from bacteria, peptidoglycan and lipoteichoic acid from Gram-positive bacteria, lipoarabinomannan from mycobacteria, zymosan from fungi, tGPI-mucin from *Trypanosoma cruzi* and the hemagglutinin protein from measles virus. TLR2 generally forms heterodimers with TLR1 or TLR6. Specifically, the TLR2-TLR1 heterodimer recognizes triacylated lipopeptides from Gram-negative bacteria and mycoplasma, whereas the TLR2-TLR6 heterodimer recognizes diacylated lipopeptides from Gram positive bacteria and mycoplasma. The synthetic DCs of the invention may be used to treat chronic infections by bacteria, fungi, parasites and viruses. The therapeutic methods of the invention may involve combined therapy with synthetic DCs of the invention and one or more lipopeptide, peptidoglycan, lipoteichoic acid, lipoarabinomannan, zymosan, tGPI-mucin and hemagglutinin protein.

TLR4 (also known as CD284; Akira, et al., *Cell* 124, 783-801 (2006)) is a cell surface protein that detects lipopolysaccharide on Gram-negative bacteria and is thus important in the activation of the innate immune system. The synthetic DCs of the invention may be used to treat chronic Gram-negative bacterial infections. The therapeutic methods of the invention may involve combined therapy with synthetic DCs of the invention and one or more bacterial lipopolysaccharides.

The synthetic DCs of the invention are preferably capable of cross presenting antigen to naïve $CD8^+$ T cells. The classical pathways of antigen processing and presentation in synthetic DCs are the exogenous pathway (involving MHC class II) and the endogenous pathway (dependent on MHC class I). $CD4^+$ T lymphocyte responses are directed by antigen presentation on MHC class II molecules, whereas $CD8^+$ CTL responses are directed by antigen presentation on MHC class I molecules. DCs are capable of taking up exogenous antigen, processing it and presenting the resulting peptides on their cell surfaces via MHC class II molecules to stimulate $CD4^+$ T lymphocyte responses. Endogenous antigens that may be derived from the synthetic DCs themselves, or from intracellular pathogens such as viruses, are processed and presented on the surfaces of the DCs via MHC class I molecules to stimulate $CD8^+$ CTLs.

$CD8^+$ CTL responses are particularly important in antiviral and anti-tumor immunity because the CTL cells are capable of killing the infected or tumor cells. However, using the classical endogenous pathway of antigen presentation, DCs will only activate CTL-based responses if they themselves become infected with the incriminating viral pathogen or become transformed. Many conventional DCs, including moDC, have very limited capacity to process and present exogenous antigens via MHC class I and thereby stimulate anti-tumor or anti-viral CTL responses.

Cross-presentation is a phenomenon whereby a limited subset of DCs is capable of taking up, processing and presenting exogenous antigen on MHC class I and thereby stimulating CTL responses. In this context, "exogenous" antigen particularly includes proteins, polypeptides or peptides (e.g. synthetic polypeptides and peptides) which are not derived from the DCs themselves. The synthetic DCs of the invention are capable of cross presenting antigen to naïve $CD8^+$ T cells. The synthetic DCs of the invention are therefore capable of taking up, processing and presenting exogenous antigen via MHC class I molecules. The cells may, therefore, be loaded or transfected with a tumor-derived or pathogen-derived antigen and used in vivo to induce CTL responses against the tumor or pathogen. This is discussed in more detail below.

The antigen, or peptides derived from it, will be presented via MHC I. Typically, the antigen may be presented by both MHC class I and MHC class II.

The ability of the synthetic DCs of the invention to cross-present antigen may be tested using any assay known in the art. The synthetic DCs of the invention may be loaded or transfected with the antigen as discussed in more detail below. The synthetic DCs of the invention are typically loaded with or cultured in the presence of a test antigen and the ability of the cells to present a peptide derived from the test antigen using MHC class I molecules is determined. Presentation may be measured by culturing the cross-presenting DCs with appropriate $CD8^+$ HLA-restricted T lymphocytes and tracking the priming of antigen-specific cells using appropriate tetramers. Alternatively, well-characterised MHC class I-restricted T cell clones of known antigen specificity may be used as a readout for cross-presentation of whole exogenous antigen. A specific assay is disclosed in the Example.

Tolerogenic DCs of the Invention

The invention also provides a synthetic DC which is tolerogenic and wherein the source DC was modified before it was used to form the iPSC to favour a tolerogenic phenotype or the synthetic DC is modified to favour a tolerogenic phenotype. This can be done as described above, such as by exposing the source DC or synthetic DC to agents such as, but not limited to, vitamin D3, dexamethasone, IL-10, TGF-β or rapamycin.

Other Features of the Synthetic DCs

A synthetic DC of the invention may be isolated, substantially isolated, purified or substantially purified. The synthetic DC is isolated or purified if it is completely free of any other components, such as culture medium, other cells of the invention or other cell types. The synthetic DC is substantially isolated if it is mixed with carriers or diluents, such as culture medium, which will not interfere with its intended use. Alternatively, the DC of the invention may be present in a growth matrix or immobilized on a surface as discussed below.

Synthetic DCs of the invention may be isolated using a variety of techniques including antibody-based techniques. Cells may be isolated using negative and positive selection techniques based on the binding of monoclonal antibodies to those surface markers which are present on the synthetic DC. Hence, the DCs may be separated using any antibody-based technique, including FACS and magnetic bead separation.

As discussed in more detail below, the synthetic DCs may be treated ex vivo. Thus the cells may be loaded or transfected with antigen and then used therapeutically in the methods of the invention. The invention therefore provides a synthetic DC of the invention loaded or transfected with an antigen. Suitable antigens are discussed below. The invention further provides a synthetic DC of the invention which comprises a nucleic acid encoding an antigen. The invention also provides a synthetic DC of the invention which has been infected by a virus particle or another vector capable of expressing an antigen.

Population of the Invention

The invention also provides a population of two or more iPSCs or synthetic DCs of the invention. Any number of cells may be present in the population.

In a preferred embodiment of the invention, the population of the invention comprises more than $5.0 \times 10^5$ DCs of the invention. The population more preferably comprises at least $5.1 \times 10^5$, at least $5.2 \times 10^5$, at least $5.5 \times 10^5$, at least $6.0 \times 10^5$, at least $6.5 \times 10^5$, at least $7.0 \times 10^5$, at least $7.5 \times 10^5$, at least $8.0 \times 10^5$, at least $8.5 \times 10^5$, at least $9.0 \times 10^5$, at least $9.5 \times 10^5$ or at least $1.0 \times 10^6$ DCs of the invention. In some instance, the population may comprise at least $1.0 \times 10^7$, at least $1.0 \times 10^8$, at least $1.0 \times 10^9$, at least $1.0 \times 10^{10}$, at least $1.0 \times 10^{11}$ or at least $1.0 \times 10^{12}$ iPSCs or DCs of the invention.

Such numbers can be achieved using the invention. Any number of iPSCs or DCs of the invention may be generated by scaling up the number of culture vessels used in the method or by using bioreactors. The scalability of the method is merely dependent on the number of source DCs and human iPSCs that may be obtained. That number is virtually unlimited. Methods for obtaining source DCs and iPSCs from humans are discussed in more detail below.

The populations of the synthetic DCs of the invention are advantageous for therapy as discussed below. This ability to produce populations comprising large numbers of DCs belonging to subsets with key characteristics, such as the cross-presentation of antigen in the case of $CD141^+$ DCs or secretion of type I interferons in the case of $CD303^+$ plasmacytoid DCs, is one of the key advantages of the invention. The invention allows the generation of sustainable populations of synthetic DCs in sufficient numbers to allow repeated cycles of effective therapy in a patient. The invention also allows the generation of sustainable populations of synthetic DCs belonging to specific subsets not normally obtainable from patients due to their anatomical distribution.

The population of the invention is preferably homologous. In other words, all of the iPSCs or DCs in the population are preferably genotypically and phenotypically identical. The population is preferably autologous. However, the population can also be semi-allogeneic. Semi-allogeneic populations are typically produced from the reprogramming and optionally re-differentiation of partially-matched, clinically-approved source DCs obtained from another patient or obtained from a public bank. In other words, all of the cells in the population are preferably genetically identical or sufficiently genetically identical that the population is immunologically compatible with a patient into which the population will be administered. Since the synthetic DCs of the invention may be derived from a patient via iPSCs, they may be autologous with the patient to be treated (i.e. genetically identical with the patient or sufficiently genetically identical that they are compatible for administration to the patient).

The population of the invention may be isolated, substantially isolated, purified or substantially purified. A population is isolated or purified if it is completely free of any other components, such as culture medium and other cells. A population is substantially isolated if it is mixed with carriers or diluents, such as culture medium, which will not interfere with its intended use. Other carriers and diluents are discussed in more detail below. A substantially isolated or substantially purified population does not comprise cells other than the iPSCs or synthetic DCs of the invention. In some embodiments, the population of the invention may be present in a growth matrix or immobilized on a surface as discussed below.

The population is typically cultured in vitro. Techniques for culturing cells are well known to a person skilled in the art. The cells are typically cultured under standard conditions of 37° C., 5% $CO_2$ in medium without serum. The cells may be cultured in any suitable flask or vessel, including wells of a flat-bottomed plate such as a standard 6 well plate. Such plates are commercially available from Fisher scientific, VWR suppliers, Nunc, Starstedt or Falcon. The wells typically have a capacity of from about 1 ml to about 4 ml. As discussed above, the number of DCs per well is typically $1.1\text{-}4.5\times10^4$ or $7.5\times10^5$. The method is typically Current Good Manufacturing Practice (cGMP) compliant. Bioreactors may also be used to scale up production.

The flask, vessel or wells within which the population is contained or cultured may be modified to facilitate handling of the iPSCs and/or synthetic DCs. For instance, the flask, vessel or wells may be modified to facilitate culture of the cells, for instance by including a growth matrix. The flask, vessel or wells may be modified to allow attachment of the iPSCs and/or synthetic DCs or to allow immobilization of the DCs onto a surface. One or more surfaces may be coated with extracellular matrix proteins such as laminin or collagen or any other capture molecules that bind to the cells and immobilize or capture them on the surface(s).

The population may be modified ex vivo using any of the techniques described herein. The population may then be used in the methods of treatment discussed in more detail below. The invention therefore provides a population of synthetic DCs of the invention loaded or transfected with an antigen or endogenously expressing the antigen. The invention further provides a population of synthetic DCs of the invention which comprise a nucleic acid encoding an antigen. The invention also provides a population of synthetic DCs of the invention which have been infected by a virus particle or another vector capable of expressing an antigen.

Method of Producing a Synthetic DC of the Invention

Conditions suitable for inducing pluripotent stem cells to differentiate into DCs are known in the art. For instance, suitable conditions for the differentiation of human ESC are disclosed in Tseng, S-Y. et al. *Regen. Med.* 4, 513-526 (2009). However, it is surprising that culturing human iPSCs under these conditions results in DCs that are capable of cross presenting an antigen to naïve $CD8^+$ T lymphocytes.

If the synthetic DCs pass through a monocytic precursor stage, the method preferably comprises (a) culturing the iPSCs in a medium comprising granulocyte macrophage-colony stimulating factor (GM-CSF) for sufficient time to produce monocytic cells, (b) culturing the monocytic cells under conditions that induce the formation of immature dendritic cells and (c) culturing the immature dendritic cells in a medium comprising growth factors that induce maturation of the DCs. This produces a mixed population containing both $CD141^+$ and $CD1c^+$ DCs. Each type may then be isolated as discussed below.

The sufficient time in step (a) is typically from 13 to 17 days. In step (a), the medium preferably further comprises one or more of stem cell factor (SCF), vascular endothelial growth factor (VEGF) and bone morphogenetic protein (BMP-4). The medium more preferably initially comprises all three of SCF, VEGF and BMP-4 and each is successively removed. Step (a) most preferably comprises initially culturing the iPSCs in a medium comprising GM-CSF, SCF, VEGF and BMP-4, removing BMP-4 from day 5 onwards, removing VEGF from day 14 onwards and removing SCF from day 19 onwards until monocytic cells are produced.

The sufficient time in step (b) is typically from 9 to 15 days. Suitable conditions for forming immature DCs from monocytic cells are known in the art. Step (b) preferably involves culturing the monocytic cells in a medium comprising GM-CSF and interleukin-4 (IL-4) for sufficient time to produce immature DCs.

Step (c) takes from 36 hours to 4 days, preferably about 2 days (48 hours). The medium in step (c) preferably comprises GM-CSF, tumor necrosis factor-α (TNFα), prostaglandin-$E_2$ ($PGE_2$), interleukin-1β (IL-1β) and interferon-γ (IFNγ).

Steps (a) to (c) typically take from 21 to 32 days.

Preferred concentrations of the various growth factors are as follows:

GM-CSF—from 25 to 75 ng/ml, more preferably 50 ng/ml;
SCF—from 10 to 30 ng/ml, more preferably 20 ng/ml;
VEGF—from 25 to 75 ng/ml, more preferably 50 ng/ml;
BMP-4—from 25 to 75 ng/ml, more preferably 50 ng/ml;
IL-4—from 10 to 150 ng/ml, more preferably 25 or 100 ng/ml;
TNFα—from 10 to 30 ng/ml, more preferably 20 ng/ml;
$PGE_2$—from 0.5 to 1.5 ng/ml, more preferably 1.0 ng/ml;
IL-1β—from 5 to 15 ng/ml, more preferably 10 ng/ml; and
IFNγ—from 10 to 20 ng/ml, more preferably 15 ng/ml.

The growth factors used in the method of the invention are typically the human forms. The growth factors used in the method of the invention are typically recombinant. The use of such factors means that the DCs of the invention are produced in clinically relevant conditions, i.e. in the absence of trace amounts of endotoxins and other environmental contaminants, such as lipoteichoic acid, lipopeptides and peptidoglycans, etc. This makes the DCs of the invention particularly suitable for administration to patients.

The method preferably further comprises isolating the synthetic DCs of the invention. Any of the methods discussed above may be used.

The invention also provides a method for producing a population of synthetic DCs of the invention that is suitable for administration to a patient, wherein the method comprises producing iPSCs from source DCs obtained from the patient and producing a population of synthetic DCs of the invention from those iPSCs using the method of the invention described above. The population will be autologous with the patient and therefore will not be rejected upon engraftment. The invention also provides a population of synthetic DCs of the invention that is suitable for administration to a patient and is produced in this manner. Alternatively, the invention provides a method for producing a population of synthetic DCs the invention that is suitable for administration to a patient, wherein the method comprises the reprogramming to pluripotency and subsequent re-differentiation of partially-matched DCs obtained from another patient or a public bank of clinically-approved samples such as umbilical cord blood.

Medicaments, Methods and Therapeutic Use

The synthetic DCs of the invention may be used in a method of therapy of the human or animal body. Thus the invention provides a synthetic DC of the invention or a population of the invention for use in a method of treatment of the human or animal body by therapy. In particular, the invention concerns using the synthetic DCs of the invention whose definitive adult phenotype facilitates the induction of a T cell response to an antigen in a patient. The antigen may be derived from a tumor or a pathogen. In one embodiment, the T cell is a cytotoxic T cell (CTL) and the induced CTL response will help to remove the tumor or the pathogen from the patient (i.e. the CTL response is therapeutic). In another embodiment, the T cell is a helper T cell (Th cell) and the induced Th response optimises the activation of CTLs in response to the antigen. In another embodiment, the T cell is a helper T cell (Th cell) and the induced Th cell response promotes humoral immunity to the antigen and optimises the production of an antibody to the antigen. In another embodiment, the T cell is a regulatory T cell (Treg cell) and the induced Treg response modulates deleterious immune responses to a self antigen or an innocuous foreign antigen.

In all instances, the synthetic DCs of the invention are preferably derived from the patient or an individual that is matched with the patient at one or more of the MHC restriction elements required for presentation of the antigen. Deriving the synthetic DCs of the invention from the patient (via source DCs and iPSCs) should ensure that the synthetic DCs are themselves not rejected by the patient's immune system. Any difference between the donor and recipient will ultimately cause clearance of the synthetic DCs, but not before they have stimulated a potent antigen-specific response.

The invention provides a method of inducing a T cell response to an antigen in a patient in need thereof, comprising administering to the patient an immunologically effective number of synthetic DCs of the invention which are loaded or transfected with the antigen, or endogenously express it, and thereby inducing a T cell response to the antigen in the patient. An immunologically effective number is a number which induces a T cell response to the antigen in the patient. The invention also provides a synthetic DC of the invention or a population of synthetic DCs of the invention for use in a method of inducing a T cell response to an antigen in a patient in need thereof, wherein the synthetic DC(s) are loaded or transfected with the antigen. The invention also provides use of a synthetic DC of the invention or a population of synthetic DCs of the invention in the manufacture of a medicament for inducing a T cell response to an antigen in a patient in need thereof, wherein the synthetic DC(s) are loaded or transfected with the antigen. The antigen may be any protein, polypeptide or peptide. Suitable antigens are discussed below with reference to tumors and pathogens. The T cell response is preferably a cytotoxic T lymphocyte (CTL) response. The CTL response is preferably a $CD8^+$ CTL response. In all embodiments, the CTL response may be therapeutic (i.e. treating a disease or condition in the patient).

In one embodiment, the antigen is a tumor antigen and the method is for treating or preventing a tumor in the patient. Hence, the invention provides a method of treating a tumor in a patient in need thereof, comprising administering to the patient a therapeutically effective number of synthetic DCs of the invention which are loaded or transfected with an antigen from the tumor and thereby inducing a T cell response to the antigen in the patient and treating the tumor. A therapeutically effective number is a number effective to ameliorate one or more symptoms of the tumor. Typically, such a number removes the tumor from the patient.

The invention also provides a synthetic DC of the invention or a population of the invention for use in a method of treating a tumor in a patient in need thereof by inducing a T cell response to an antigen from the tumor in the patient, wherein the synthetic DC(s) are loaded or transfected with the antigen. The invention also provides use of a synthetic DC of the invention or a population of synthetic DCs of the invention in the manufacture of a medicament for treating a tumor in a patient in need thereof by inducing a T cell response to an antigen from the tumor in the patient, wherein the synthetic DC(s) are loaded or transfected with the antigen.

Tumors from which the antigen may be derived include, but are not limited to, melanoma, lymphoma and leukaemia or tumors of the lung, liver, pancreas, prostate, breast, colon and ovary. Suitable tumor antigens include, but are not limited to, Melan-A, tyrosinase, p97, beta-HCG, GalNAc, MAGE-1, MAGE-2, MAGE-4, MAGE-12, MUC1, MUC2, MUC3, MUC4, MUC18, CEA, DDC, P1A, EpCam, melanoma antigen gp75, Hker 8, high molecular weight melanoma antigen, K19, Tyr1, Tyr2, members of the pMel 17 gene family, c-Met, PSA (prostate antigen), PSM (prostate mucin antigen), PSMA (prostate specific membrane antigen), prostate secretary protein, alpha-fetoprotein, CA125, CA19.9, TAG-72, BRCA-1 and BRCA-2 antigens. If the invention concerns treating a tumor in a patient, the antigen is preferably obtained from the tumor itself, for instance extracted by biopsy to and identified in vitro. In another embodiment, the antigen is a recombinant protein available commercially. Such antigens include, but are not limited to those tumor antigens listed above.

In another embodiment, the antigen is from a pathogen and the method is for treating an infection by the pathogen in the patient. Hence, the invention provides a method of treating a chronic pathogenic infection in a patient in need thereof, comprising administering to the patient a therapeutically effective number of synthetic DCs of the invention which are loaded or transfected with an antigen from the pathogen and thereby inducing a T cell response to the antigen in the patient and treating the infection. A therapeutically effective number is a number effective to ameliorate one or more symptoms of the infection. Typically, such a number removes the pathogen from the patient.

The invention also provides a synthetic DC of the invention or a population of synthetic DCs of the invention for use in a method of treating a chronic pathogenic infection in a patient in need thereof by inducing a T cell response to an antigen from the pathogen in the patient, wherein the synthetic DC(s) are loaded or transfected with the antigen. The invention also provides use of a synthetic DC of the invention or a population of synthetic DCs of the invention in the manufacture of a medicament for treating a pathogenic infection in a patient in need thereof by inducing a T cell response to an antigen from the pathogen in the patient, wherein the synthetic DC(s) are loaded or transfected with the antigen. Suitable pathogens that may be treated or prevented in accordance with the invention include, but are not limited to, bacteria, such as *Mycobacterium tuberculosis*, viruses, such as HIV, parasites and protozoa, such as *Plasmodium falciparum* and fungi. Typically, such microorganisms will establish chronic infections that are resistant to conventional treatment.

In another embodiment, the method is for removing immunological tolerance to the antigen. The antigen is typically a self antigen such as a tumor antigen. The antigen may be any of the tumor antigens discussed above. One of the main barriers to inducing an effective immune response to tumor antigens is self tolerance since tumor antigens are self molecules rather than pathogen derived. This self tolerance is often maintained by regulatory T cells (Treg) specific for the antigens which inhibit the priming of effector T cells specific for the same antigens. Nevertheless, Treg are relatively unstable and may, in response to IL-6, convert to Th17 cells, which are strongly pro-inflammatory. Th17 cells secrete IL-17. Since the synthetic DCs of the invention secrete high levels of IL-6 upon maturation, they are capable of bypassing the Treg barrier, converting Treg to Th17 cells and thereby removing immunological tolerance to the antigen.

In another embodiment, the invention provides a method of inducing tolerance to an antigen in a patient in need thereof, comprising administering to the patient an immunologically effective number of tolerogenic DCs of the invention and thereby inducing tolerance to the antigen in the patient, wherein the DCs are loaded or transfected with the antigen or endogenously express the antigen.

The invention also provides a tolerogenic DC or a population of tolerogenic DCs of the invention for use in a method of inducing tolerance to an antigen in a patient in need thereof, wherein the DC(s) are loaded or transfected with the antigen, or endogenously express the antigen. The invention also provides use of a tolerogenic DC or a population of tolerogenic DCs of the invention in the manufacture of a medicament for inducing tolerance to an antigen in a patient in need thereof, wherein the tolerogenic DC(s) are loaded or transfected with the antigen, or endogenously express the antigen. The antigen is preferably involved in an autoimmune disease in the patient or will facilitate cell or enzyme replacement therapy for the correction of a congenital condition in the patient.

Immunisation results in promoting an immune response against the chosen antigen. Any of the effects resulting from the loaded or transfected synthetic DCs mentioned herein may be promoted or achieved. In particular, the level of presentation of the chosen antigen will be increased in the patient. An increase in presentation via MHC I and/or MHC II molecules and in particular via MHC I molecules in the patient will typically be seen. In a preferred case, the level of antigen presentation achieved may be such that when the same antigen is encountered again an increased immune response is seen in comparison to the situation in which the initial immunisation had not taken place. In particular, a therapeutic and/or protective immune response is raised. The invention may, therefore, ensure that a higher level of immune response is seen when the antigen is next encountered, for instance, upon serial administration of the population of synthetic DCs, in order to further boost responses to the antigen.

The invention may be used to enhance the level of antigen presentation or of any of the downstream effects thereof, such as any of those mentioned herein, in comparison to administration of an equivalent amount of antigen in the absence of loaded or transfected synthetic DCs. The increase may be double, treble, or more fold, in some cases it may be at least ten-fold, preferably at least twenty-fold and even more preferably at least 100 fold, or 1000 fold or more. It may be that a therapeutic response is seen whereas, in the absence of the use of loaded or transfected synthetic DCs, it is not.

The loaded or transfected synthetic DCs may be administered to any suitable patient. The patient is generally a human patient. The patient may be an infant, a juvenile or an adult. In one embodiment, the patient is susceptible to, or at risk from, the relevant disease. For instance, the patient may be genetically predisposed to developing the tumor. Alternatively, the patient may have been exposed, or will be in a region where there is a risk of exposure, to a particular antigen and in particular a pathogen, for example, the vertical transmission of HIV-1 from mother to child.

The invention may be used in combination with other means of, and substances for, immunisation. In some cases the loaded or transfected synthetic DCs may be administered simultaneously, sequentially or separately with antigen which is not present in loaded or transfected DCs (i.e. free antigen). The loaded or transfected synthetic DCs may be used in combination with existing vaccines for a particular antigen and may, for example, be simply mixed with such vaccines. Thus the invention may be used to increase the efficacy of existing vaccines including, for example, peptide, polypeptide, protein, nucleic acid, viral and/or bacterial based antigens.

In a preferred embodiment, the loaded or transfected synthetic DCs are administered simultaneously, sequentially or separately with one or more ligands of the pattern recognition receptors (PRRs) or TLRs. This will improve the ability of the DCs to cross present antigen in vivo. Suitable ligands include, but are not limited to, 2'-deoxyribo(cytidine-phosphoguanosine) (CpG) DNA motifs, polyinosinic-polycytidylic acids (poly(I:Cs)), lipopeptides, peptidoglycans, lipoteichoic acid, lipoarabinomannan, zymosan, tGPI-mucin, hemagglutinin protein and lipopolysaccharides.

The invention concerns the use of loaded or transfected synthetic DCs. The synthetic DCs may be loaded or transfected using any method known in the art. The loading of synthetic DCs may be performed in vitro or ex vivo. In each case, the synthetic DCs may simply be in contact with the antigen in culture. The synthetic DCs of the invention are capable of endocytosing, phagocytosing or otherwise taking up exogenous peptide, polypeptide or protein antigens and, after internalisation and processing, presenting antigenic peptide fragments on their surface, bound to products of the MHC. Alternatively, the synthetic DCs may be loaded with antigen by conjugating it to monoclonal antibodies specific for surface molecules, such as CD205 and DNGR-1. Such molecules are known in the art.

The transfection of synthetic DCs may be performed in vitro or ex vivo. Alternatively, stable transfection may be performed at the iPSC stage allowing DCs expressing the transgene to be differentiated from them. The synthetic DCs are transfected with a nucleic acid encoding the antigen. For instance, viral particles or other plasmid vectors encoding the antigen may be employed. Methods for doing this are known in the art.

The nucleic acid gives rise to expression of the antigen in the synthetic DCs and to the subsequent presentation of the antigen by the cells. The nucleic acid molecule will preferably comprise a promoter which is operably linked to the sequences encoding the antigen and which is active in the synthetic DCs or which can be induced in the synthetic DCs.

In a particularly preferred embodiment, the nucleic acid encoding the antigen may be delivered via a viral particle. The viral particle may comprise a targeting molecule to ensure efficient transfection. The targeting molecule will typically be provided wholly or partly on the surface of the virus in order for the molecule to be able to target the virus to the synthetic DCs.

Any suitable virus may be used in such embodiments. The virus may, for example, be a Sendai virus, a retrovirus, a lentivirus, an adenovirus, an adeno-associated virus, a vaccinia virus or a herpes simplex virus. In a particularly preferred embodiment the virus may be a lentivirus. The lentivirus may be a modified HIV virus suitable for use in delivering genes. The lentivirus may be a SIV, FIV, or equine infectious anemia virus (EQIA) based vector. The virus may be a moloney murine leukaemia virus (MMLV). The viruses used in the invention are preferably replication deficient.

Viral particles do not have to be used. Any vector capable of transfecting the synthetic DCs of the invention may be used, such as conventional plasmid DNA or RNA transfection.

The nucleic acid molecule may also encode other sequences, for example the nucleic acid may comprise sequences which express proteins which boost the immune response to the antigen. The nucleic acid may encode a cytokine, including any of those mentioned herein and in particular IL-1, IL-2 and/or IL-12. The nucleic acid may also encode a costimulatory molecule such as a cell-surface molecule which enhances the immune response. The nucleic acid may encode, for example, CD80 and/or CD86. The nucleic acid molecule preferably encodes one or more of the Toll-like receptor ligands disclosed herein.

Uptake of nucleic acid constructs may be enhanced by several known transfection techniques, for example those including the use of transfection agents. Examples of these agents includes cationic agents, for example, calcium phosphate and DEAE-Dextran and lipofectants, for example, lipofectAmine, fugene, TransIT-LT1 and transfectam.

The cell may be loaded or transfected under suitable conditions. The cell and antigen or vector may, for example, be in contact for between five minutes and ten days, preferably from an hour to five days, more preferably from five hours to two days and even more preferably from twelve hours to one day.

The invention also provides synthetic DCs which have been loaded or transfected with an antigen. Such synthetic DCs may be used in the therapeutic embodiments of the invention. The loaded or transfected cells may comprise epitopes of the antigen. The cells may also comprise a targeting molecule and/or breakdown products thereof. The invention provides such cells in an isolated form as discussed above. The transfected cells may comprise a nucleic acid encoding the antigen and, in particular, may comprise a viral vector encoding the antigen. Preferably, the viral vector will be replication deficient.

Generally the loaded or transfected synthetic DCs carry peptides, and in particular an antigenic epitope derived from the chosen antigen on their surface in conjunction with an MHC class I or class II molecule and in particular in conjunction with an MHC I molecule. In one embodiment each DC has at least 100, preferably at least 200, for example at least or about 500 or 1000, class I and/or class II molecules on its surface loaded with the product and in particular class I molecules. In some cases, the synthetic DCs may carry a label or be labelled, such as, for example, with a fluorescent molecule such as green fluorescent protein (GFP).

In some embodiments, source DCs may be recovered from the patient, converted into synthetic DCs using the invention, loaded or transfected in vitro and then returned to the same subject. In such instances, the synthetic DCs employed in the invention, will be autologous cells and fully matched with the patient for MHC class I HLA-A or HLA-B; and/or for MHC class II type. In a preferred case, the cells employed in the invention are recovered from a patient and utilised ex vivo and subsequently returned to the same patient.

In another embodiment, source DCs may be isolated from another patient or cultured from a public bank of clinically-approved samples in order to ensure that they share with the patient one or more MHC molecules required for presentation of the designated antigen to the immune system of the recipient.

Pharmaceutical Compositions, Vaccines and Administration

The invention additionally provides a pharmaceutical composition comprising (a) a synthetic DC of the invention or a population of synthetic DCs of the invention and (b) a pharmaceutically acceptable carrier or diluent. The present invention also provides a vaccine composition comprising a synthetic DC or population of synthetic DCs of the invention. The vaccines and compositions may comprise any of the synthetic DCs or populations mentioned herein and, in come embodiments, the nucleic acid molecules, vectors, viruses or antigens described herein. The invention provides a method of vaccination comprising administering to a patient an effective amount of a vaccine composition of the invention.

The various compositions and vaccines of the invention may be formulated using any suitable method. Formulation of cells with standard pharmaceutically acceptable carriers and/or excipients may be carried out using routine methods in the pharmaceutical art. The exact nature of a formulation will depend upon several factors including the cells to be administered and the desired route of administration. Suitable types of formulation are fully described in Remington's Pharmaceutical Sciences, 19$^{th}$ Edition, Mack Publishing Company, Eastern Pennsylvania, USA.

The cells may be administered by any route. Suitable routes include, but are not limited to, intravenous, intramuscular, intraperitoneal or other appropriate administration routes. The cells are preferably administered to sites of antigen presentation, such as draining lymph nodes.

Compositions and vaccines may be prepared together with a physiologically acceptable carrier or diluent. Typically, such compositions and vaccines are prepared as liquid suspensions of cells. The cells may be mixed with an excipient which is pharmaceutically acceptable and compatible with the active ingredient. Suitable excipients are, for example, water, saline, dextrose, glycerol, or the like and combinations thereof.

In addition, if desired, the vaccine and/or pharmaceutical compositions of the invention may contain minor amounts of auxiliary substances such as wetting or emulsifying agents, pH buffering agents, and/or adjuvants which enhance effectiveness.

In some embodiments, the pharmaceutical composition or vaccine may comprise an adjuvant. In other words, an adjuvant may be present in the various formulations of the invention or be administered simultaneously, separately or sequentially with them. Suitable adjuvants include, for example, any substance that enhances the immune response of the subject to the antigen (including when delivered by the polynucleotide of the invention). They may enhance the immune response by affecting any number of pathways, for example, by stabilizing the antigen/MHC complex, by causing more antigen/MHC complex to be present on the cell surface, by enhancing maturation of DCs, or by prolonging the life of APCs (e. g., inhibiting apoptosis).

Examples of adjuvants that may be employed include cytokines. Certain cytokines, for example TRANCE, flt-3L, or agents such as CD40L, enhance the immunostimulatory capacity of antigen presenting cells and may be employed. Non-limiting examples of cytokines which may be used alone or in combination include, interleukin-2 (IL-2), interleukin-3 (IL-3), interleukin 6 (IL-6), interleukin-12 (IL-12), G-CSF, granulocyte macrophage-colony stimulating factor (GM-CSF), interleukin-la (IL-la), interleukin-11 (IL-11), c-kit ligand, thrombopoietin (TPO), CD40 ligand (CD40L; also known as CD154), tumor necrosis factor-related activation-induced cytokine (TRANCE) and flt3 ligand (flt-3L). Further examples of adjuvants which may be effective include but are not limited to: aluminium hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion. Especially preferred adjuvants include the ligands of the pattern recognition receptors discussed above.

In cases where the invention uses synthetic DCs transfected with a nucleic acid which encodes an antigen, the nucleic acid may also encode molecules capable of acting as an adjuvant. Thus the nucleic acid may lead to the production of any of the adjuvants mentioned herein and in particular a cytokine or costimulatory molecule. The cytokine may, for example be, IL-1, IL-2, and/or IL-12 which will preferably be secreted from the antigen presenting cell. The costimulatory molecule may, for example, be CD80 or CD86 which will be preferably expressed on the cell surface of the synthetic DCs.

The synthetic DCs are administered in a manner compatible with the dosage formulation and in such amount will be immunologically, prophylactically and/or therapeutically effective. The quantity to be administered depends on the subject to be treated, capacity of the subject's immune system to respond to the antigen, and the degree of CTL response desired. Precise amounts of synthetic DCs required to be administered may depend on the judgment of the practitioner and may be peculiar to each subject.

The methods described herein are preferably carried out in conjunction with standard chemotherapy or radiotherapy. Such therapies have been shown to act synergistically with cell vaccination strategies, such as the methods of the invention. Dying tumor cells release a source of the tumor antigens helping to sustain the immune response generated by cell vaccination.

Any suitable number of cells may be administered to a subject. For example, at least, or about, $10^5$, $10^6$, $10^7$, $10^8$, $10^9$ cells may be administered. As a guide, the number of cells of the invention to be administered may be from $10^5$ to $10^9$, preferably from $10^6$ to $10^8$. Any of the specific numbers discussed above with reference to the populations of the invention may be administered. In such cases where cells are administered or present, culture medium may be present to facilitate the survival of the cells. In some cases the cells of the invention may be provided in frozen aliquots and substances such as DMSO may be present to facilitate survival during freezing. Such frozen cells will typically be thawed and then placed in a buffer or medium either for maintenance or for administration. In some cases the synthetic DCs of the invention may first be irradiated or otherwise rendered post-mitotic to mitigate any risks of tumorigenesis that might arise from the accidental carryover of undifferentiated iPSCs into the inoculum.

The following Examples illustrate the invention.

Example 1

FIGS. 1-4 demonstrate the utility of the invention for the production of synthetic DCs displaying a definitive adult phenotype rather than a primitive fetal or neonatal phenotype. Since cell types cultured from mouse pluripotent stem cells are peculiarly susceptible to a blockage in their differentiation beyond a primitive phenotype, mouse bone marrow derived DCs (bmDCs) were employed as the source material. Magnetic bead separation was used to purify classical CD11c$^+$ DCs from mixed populations of hematopoietic cells cultured in vitro from bone marrow progenitors for 7 days in GM-CSF (FIG. 1A). Purified cells displayed the anticipated veiled morphology of terminally differentiated DCs (FIG. 1B), expressed surface MHC class II, CD80 and CD54 (FIG. 1C) and stimulated proliferative responses among naïve allogeneic T cells (FIG. 1D), a functional assay capable of distinguishing DCs from other cell types and populations of antigen presenting cells.

Figure 2A:
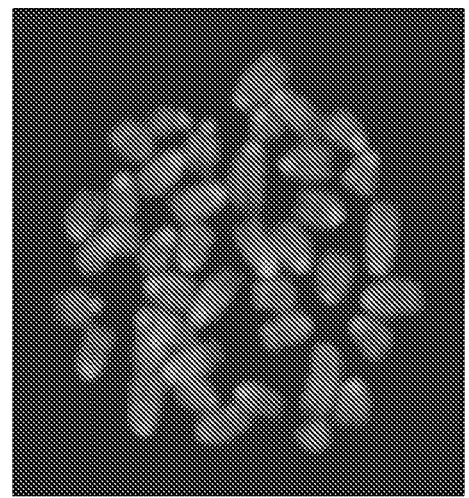
FIG. 2: Characterisation of iPSC reprogrammed from source DCs. Reprogramming of source DCs results in the appearance of typical iPSC colonies consisting of cells with prominent nuclei, characteristic of pluripotent cells (A). Lines of iPSC established from source DCs are karyotypically normal (B) and express the pluripotency markers Oct3/4, Nanog and SSEA-1 (C). Upon differentiation in vitro, iPSC derived from source DCs spontaneously form embryoid bodies (D) which, when implanted under the kidney capsule of syngeneic recipient mice, form teratomas containing tissues derived from each of the three embryonic germ layers, as evidence of their pluripotency (E).
Figure 2B:
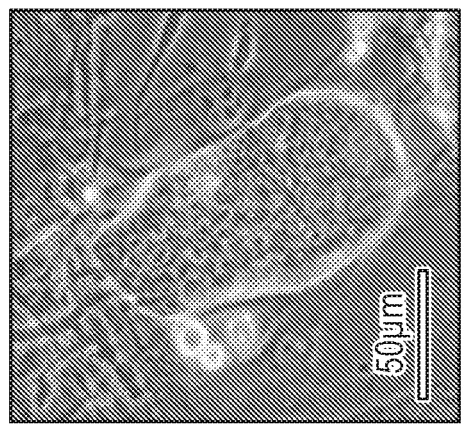
Figure 2C:
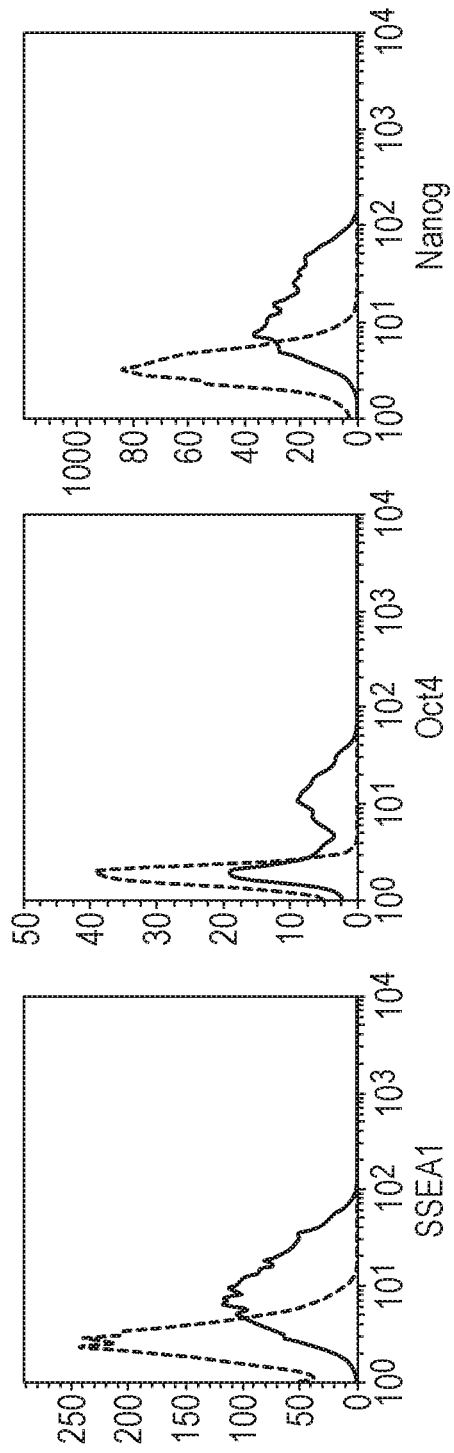
Figure 2D:
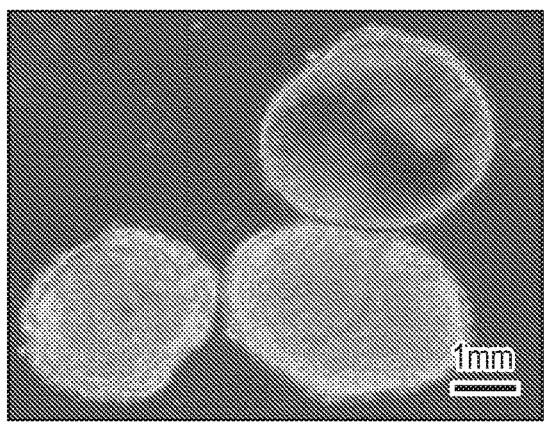
Figure 2E:
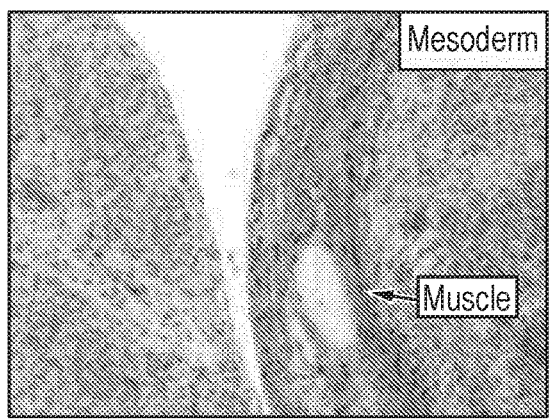
Figure 2F:
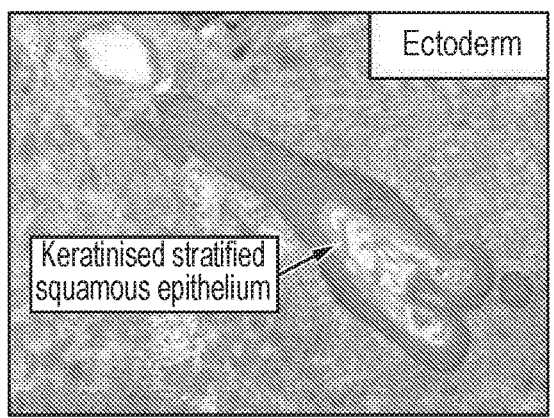
Figure 2G:
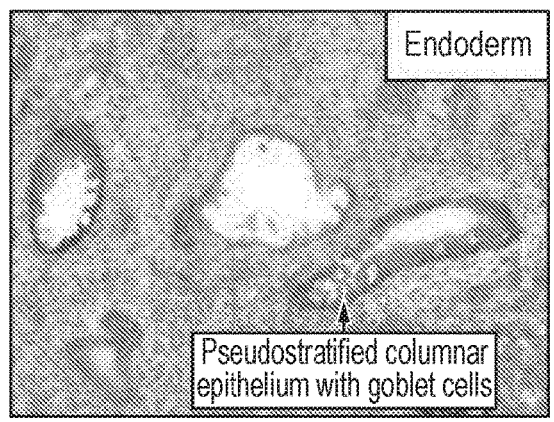

Purified source DCs were reprogrammed to pluripotency using a Sendai virus system for the transient introduction of reprogramming factors. Colonies appearing 9 days after transduction, contained cells displaying the characteristic morphology of pluripotent cells, including prominent nuclei and nucleoli (FIG. 2A). Cell lines established from these colonies were found to be karyotypically normal (FIG. 2B) and expressed conventional markers of pluripotency, including the cell surface protein SSEA-1 and the transcription factors Oct 4 and Nanog (FIG. 2C). Upon differentiation in vitro, iPSC spontaneously formed embryoid bodies (FIG. 2D) which produced teratomas when implanted under the kidney capsule of syngeneic recipient mice. Teratomas contained a wide variety of cell types and tissues including smooth muscle of mesodermal origin (FIG. 2E), cornified epithelium from the ectoderm (FIG. 2F) and endodermal tissues, such as gut epithelium (FIG. 2G), thereby confirming that reprogramming of source DCs had achieved an unequivocal state of pluripotency.

Figure 3A:
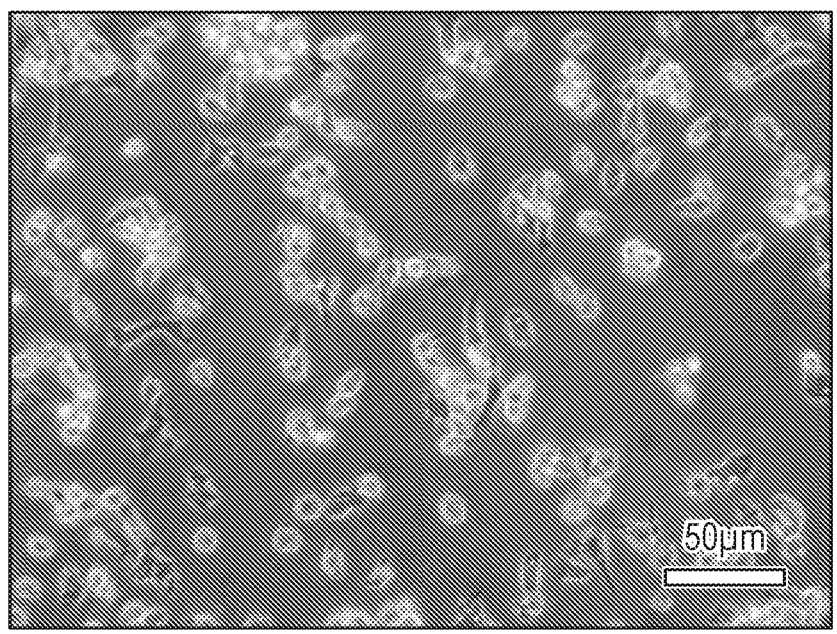
FIG. 3: Differentiation of synthetic DCs from iPSC. Directed differentiation of iPSC derived from source DCs yields large numbers of immature synthetic DCs (A) which adopt a highly veiled and dendritic morphology upon maturation (B). Maturation induces the up-regulation of MHC class II and the co-stimulatory molecules CD40, CD54, CD80 and CD86 (C). Immature synthetic DCs process the soluble protein antigen, hen egg lysozyme (HEL) and present it to an antigen-specific T cell hybridoma (D). Exposure of synthetic DCs to the TLR4 ligand LPS induces the secretion of IL-12 in a dose-dependent manner (E).
Figure 3B:
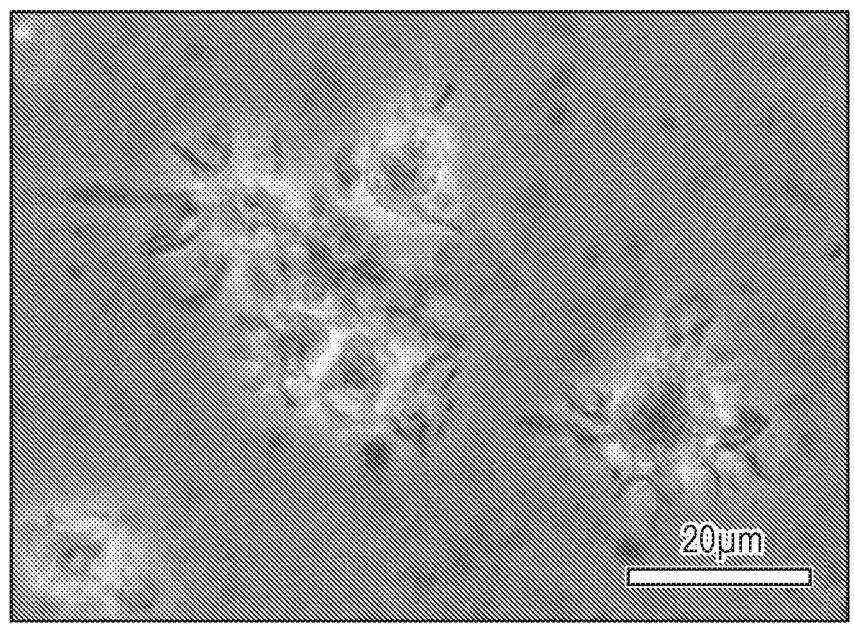
Figure 3D:
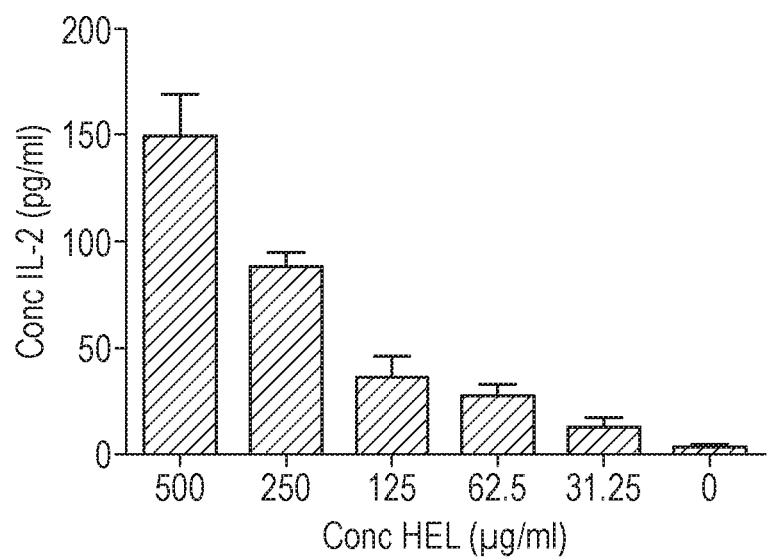
Figure 3E:
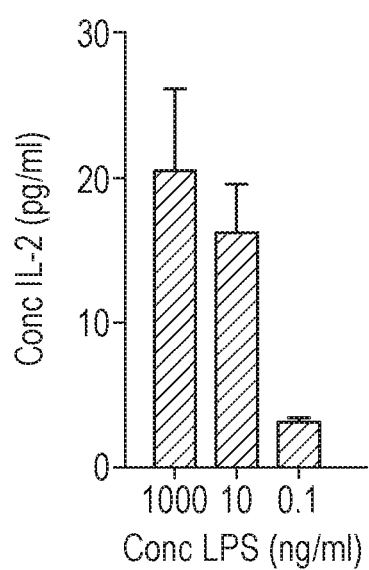

Directed differentiation of iPSCs derived from source DCs confirmed their ability to readily re-differentiate along the DC lineage to produce large numbers of immature DCs (FIG. 3A) which adopted a highly dendritic morphology upon maturation (FIG. 3B) and displayed the cardinal features of definitive adult DCs. In particular, synthetic DCs expressed the anticipated profile of surface molecules, including MHC class II and the co-stimulatory molecules CD40, CD54, CD80, and CD86, all of which were significantly up-regulated upon maturation in response to LPS (FIG. 3C). Synthetic DCs were also able to process and present the conventional foreign antigen, hen egg lysozyme (HEL) to an antigen specific T cell hybridoma (FIG. 3D) and secreted IL-12 in a dose-dependent fashion, upon challenge with LPS (FIG. 3E), suggesting that they had overcome the profound blockage in IL-12 secretion evident among fetal or neonatal DCs.

Figure 4A:
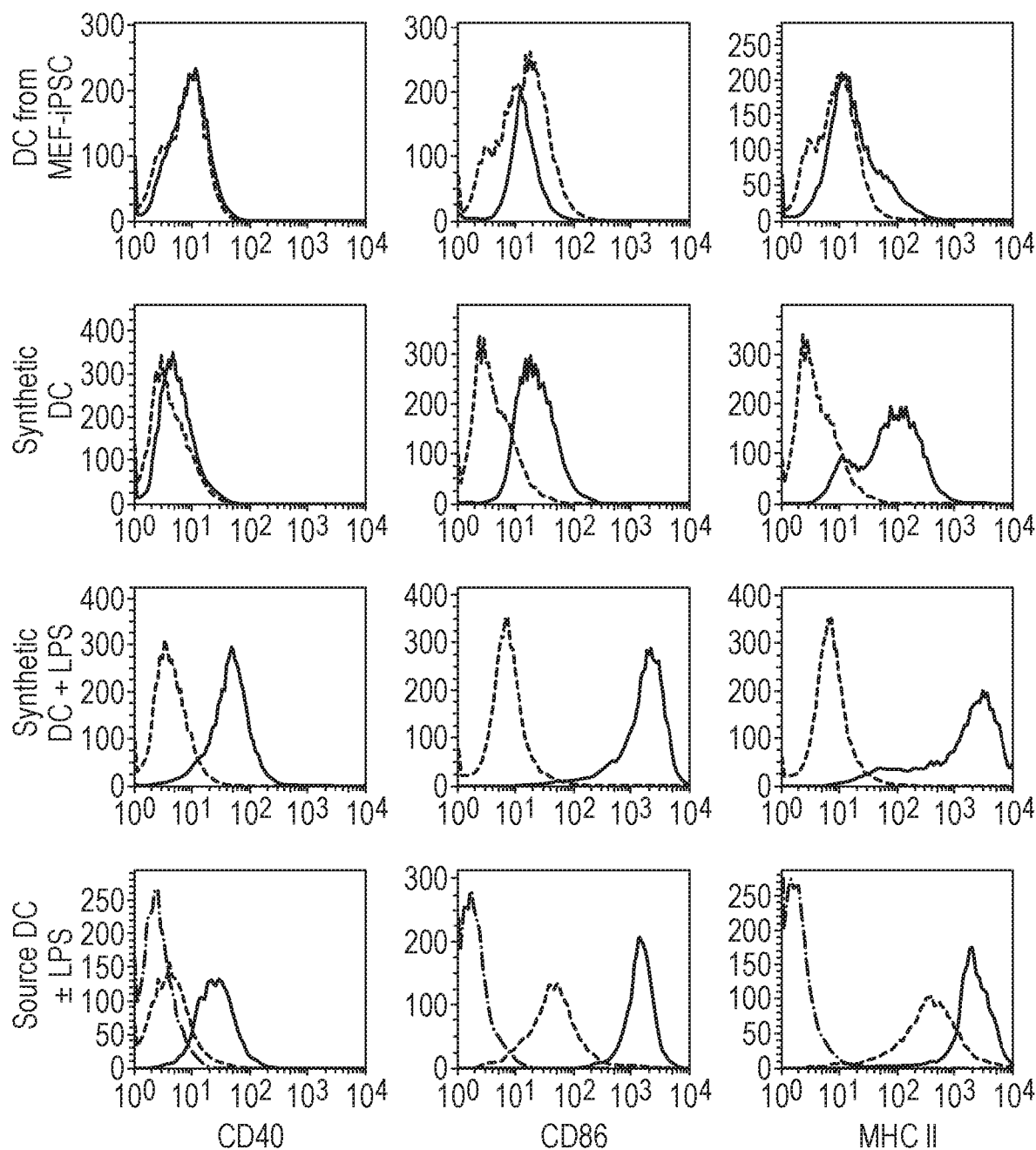
FIG. 4: Comparison between synthetic DCs, source DCs and DCs differentiated from iPSC derived from conventional mouse embryonic fibroblasts (MEF). (A) Constitutive expression of MHC class II and CD86 by immature synthetic DCs is significantly higher than their counterparts differentiated from MEF-derived iPSC and is up-regulated upon maturation in response to LPS, making their expression profile comparable to that of source DC (red histograms: expression of markers by mature source DC; orange histograms: expression levels of immature cells; blue histograms: background staining by isotype matched controls). (B) A greater proportion of embryoid bodies from iPSC derived from source DCs produce synthetic DCs and do so more rapidly than those derived from conventional iPSC. Synthetic DCs secrete IL-12 following exposure to LPS, unlike their counterparts differentiated from conventional iPSC lines (C), but secrete significantly lower levels of IL-10 (D), a cytokine profile comparable to source DCs. The immunogenic phenotype of synthetic DCs is evident from their enhanced stimulation of the allogeneic mixed leukocyte reaction (E).
Figure 4B:
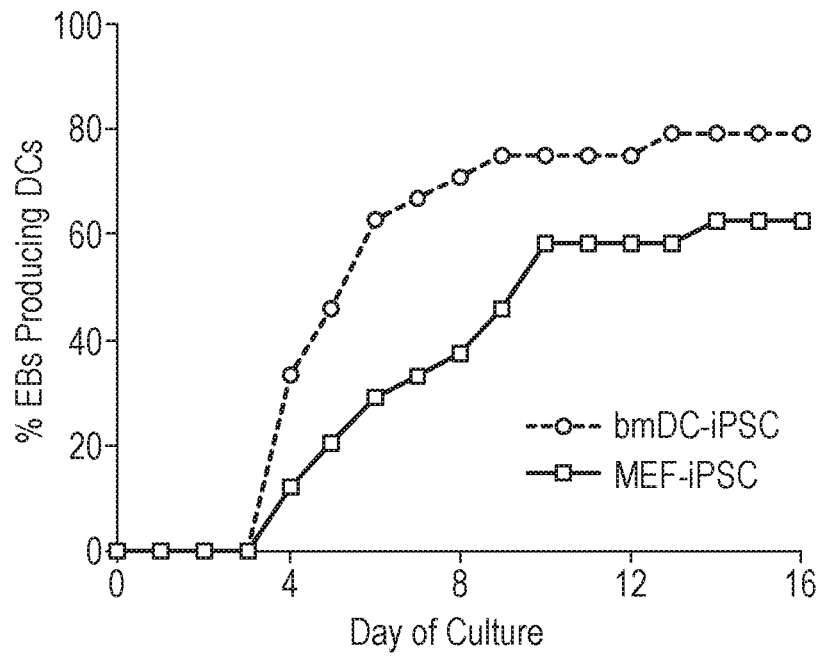
Figure 4C:
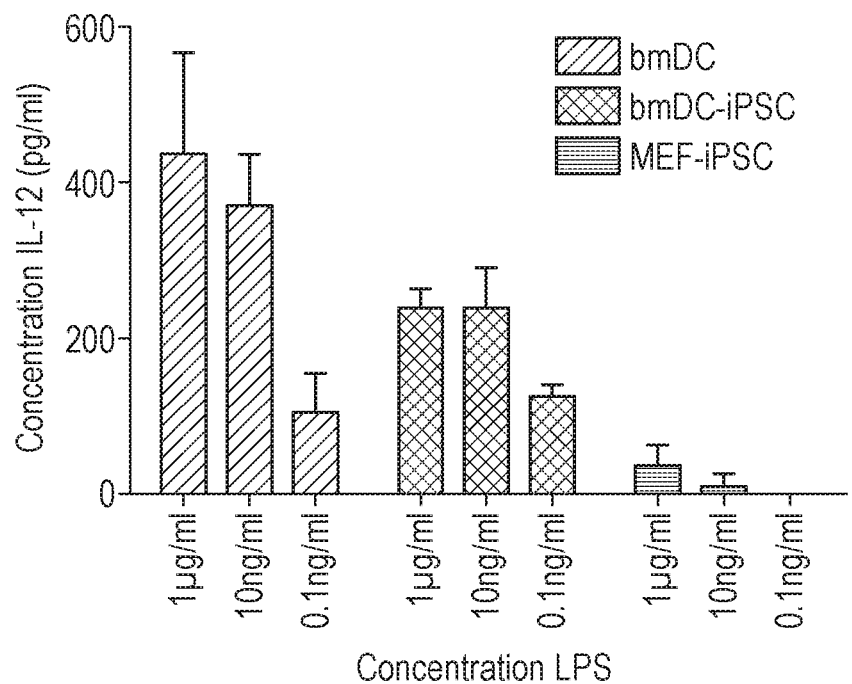
Figure 4D:
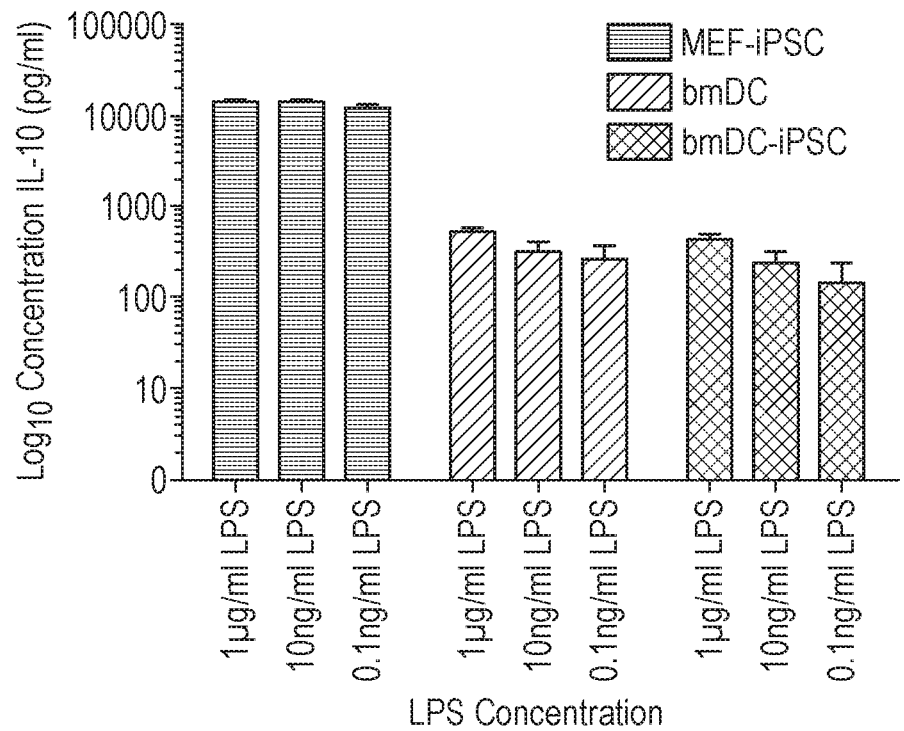
Figure 4E:
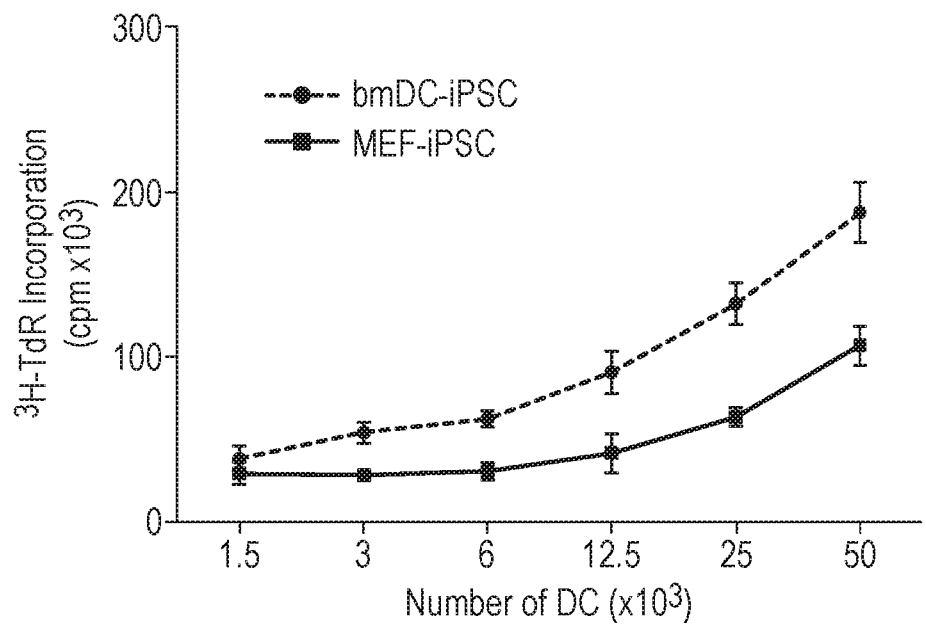

A careful comparison between synthetic DCs of the invention and either source DCs or DCs differentiated from conventional iPSC derived from mouse embryonic fibroblasts (MEFs), revealed that they are more comparable to source DCs with respect to their surface phenotype (FIG. 4A), and cytokine profile. In particular, synthetic DCs of the invention were found to secrete high levels of IL-12 (FIG. 4C) and low IL-10 (FIG. 4D), while their counterparts differentiated from conventional MEF-derived iPSCs produced barely detectable levels of IL-12 but secreted 10-fold higher concentrations of IL-10, a pro-tolerogenic phenotype typical of primitive fetal or neonatal DCs. Accordingly, synthetic DCs of the invention consistently exhibited higher immunogenicity in the allogeneic mixed leukocyte reaction than their counterparts differentiated from MEF-derived iPSCs (FIG. 4E).

Example 2

Figure 5A:
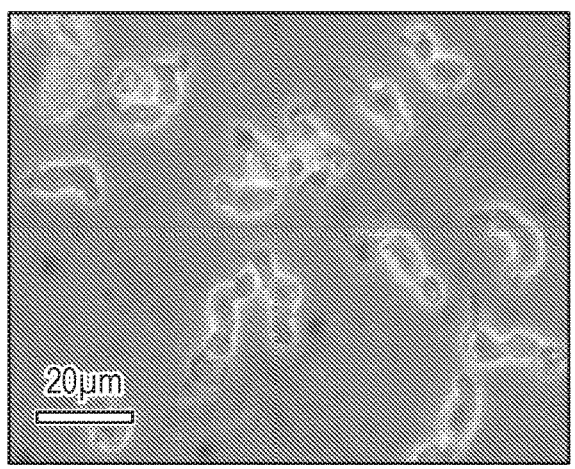
FIG. 5: Characterisation of source DC differentiated from human peripheral blood monocytes. Monocytes were purified from the peripheral blood of a healthy volunteer using MACS selection of CD14$^+$ cells (A). Monocytes cultured in rhGM-CSF and IL-4 for 7 days produced a homogenous population of DC (B) with classical dendritic morphology (C, inset) and expression of the surface markers CD11c, HLA-DR and CD40 (D).
Figure 5B:
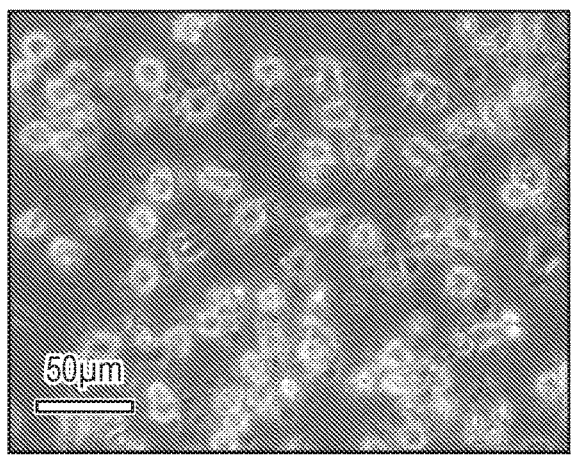
Figure 5C:
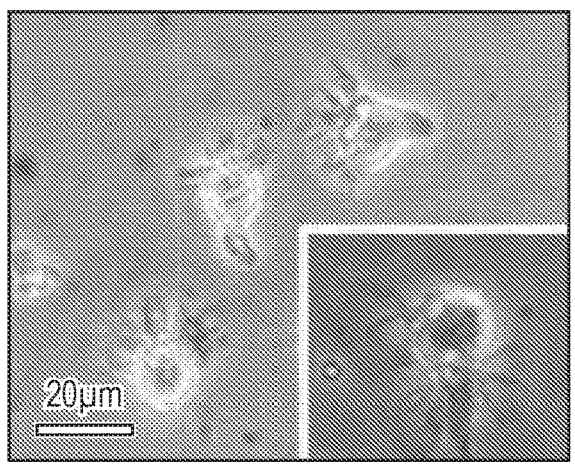
Figure 5D:
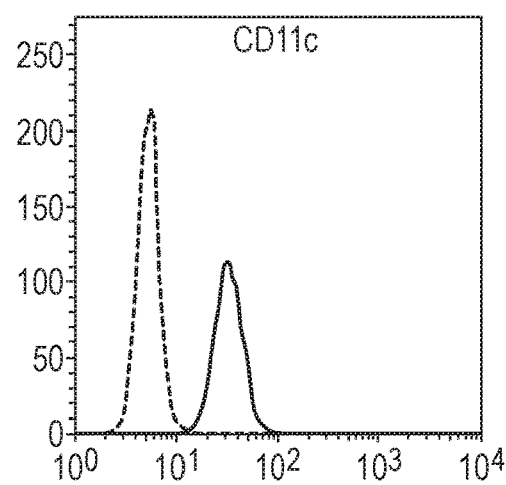
Figure 5D:
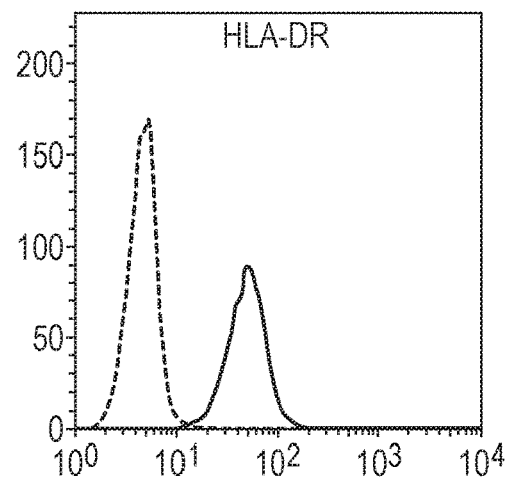
Figure 5D:
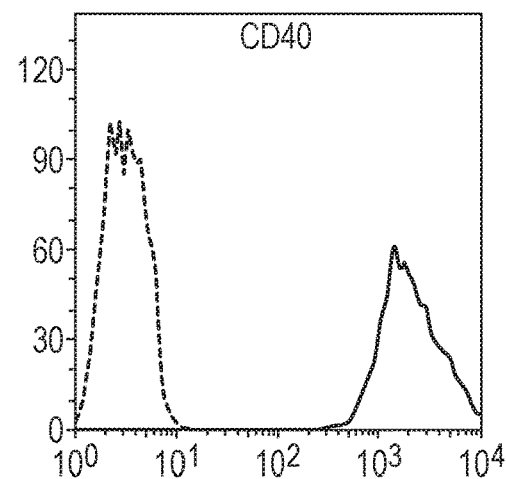

To demonstrate the utility of the invention for cells of human origin, peripheral blood was taken from a healthy, HLA-A*0201+ volunteer and monocytes were purified using CD14-microbeads (Miltenyi Biotec) (FIG. 5A). Monocytes were cultured for 7 days in recombinant human GM-CSF and IL-4 to generate a homogenous population of source DCs (FIG. 5B), displaying typical dendritic morphology at high magnification (FIG. 5C), including extensive veils of cytoplasm (inset). Source DC expressed the DC-specific marker CD11c as well as HLA-DR and CD40 (FIG. 5D).

Figure 6A:
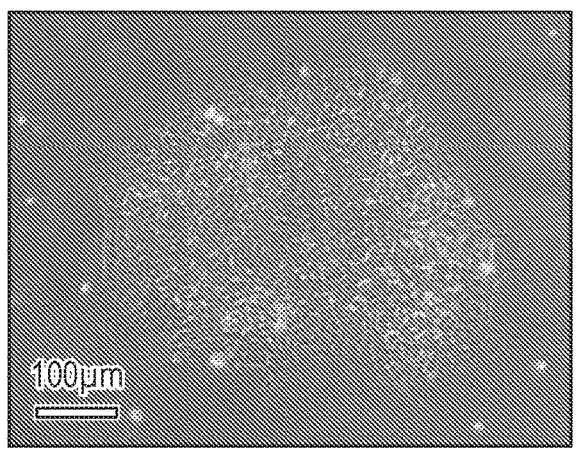
FIG. 6: Characterisation of iPSC reprogrammed from human monocyte-derived DC. Typical colony (A) and cell morphology (B) of a representative iPSC line (C3). C: Intracellular expression of NANOG and OCT4 and surface expression of SSEA-4 by two independent iPSC lines (C3 and C5), indicative of their pluripotent state.
Figure 6B:
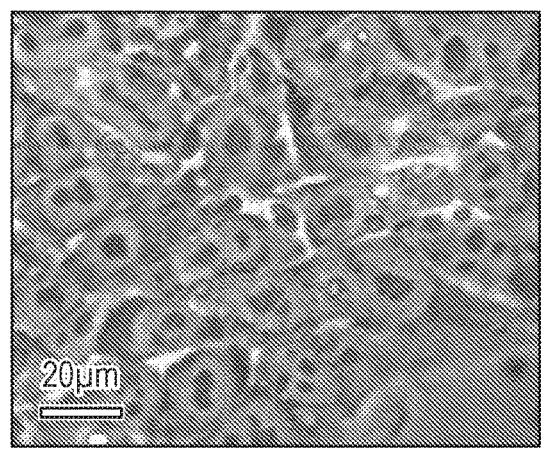
Figure 6C:
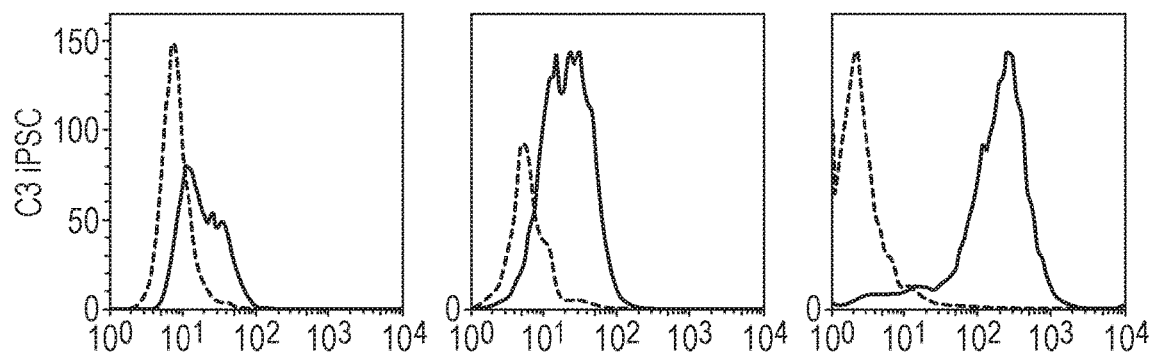

Source DC were reprogrammed using Sendai virus (Cytotunes II) as a vehicle for the delivery of pluripotency genes. Cells were plated onto mitotically-inactivated mouse embryonic fibroblast feeder cells and cultured until the appearance of colonies which were subsequently maintained in a clonal fashion and passaged on matrigel-coated plates. Several iPSC lines were derived showing classical colony morphology (FIG. 6A) together with the high nucleus to cytoplasm ratio typical of pluripotent cells and highly distinctive nucleoli under high magnification (FIG. 6B). Intracellular staining for NANOG and OCT4 showed expression of either transcription factor in the two distinct iPSC lines, C3 and C5. Likewise, expression of the surface marker SSEA-4 was consistent with a pluripotent phenotype (FIG. 6C).

Figure 7A:
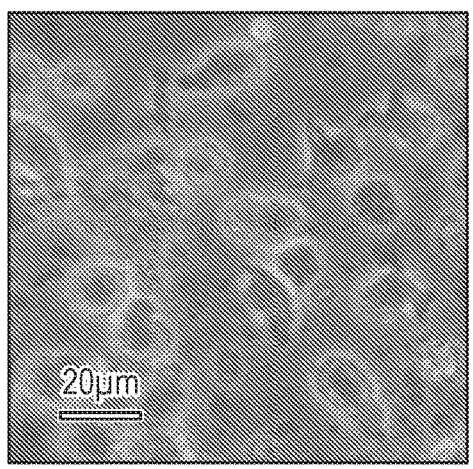
FIG. 7: Capacity of iPSC reprogrammed from human monocyte-derived DC, to re-differentiate along the DC pathway. (A) Photomicrograph of non-adherent cells shed from EBs cultured with appropriate growth factors over a 3 week period. Cells contain a population of CD11c$^+$ DC (B) expressing an immature phenotype, but capable of maturation in response to inflammatory cytokines (C).
Figure 7B:
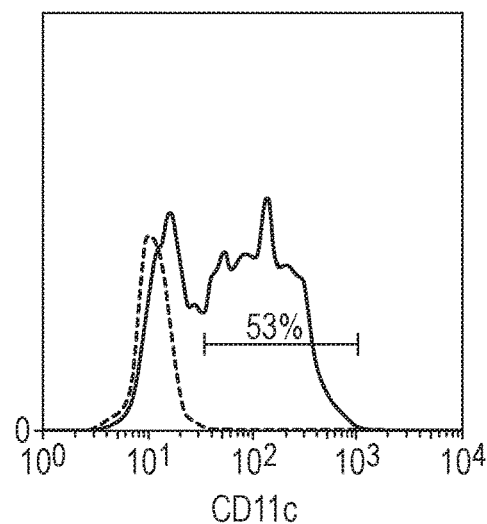
Figure 7C:
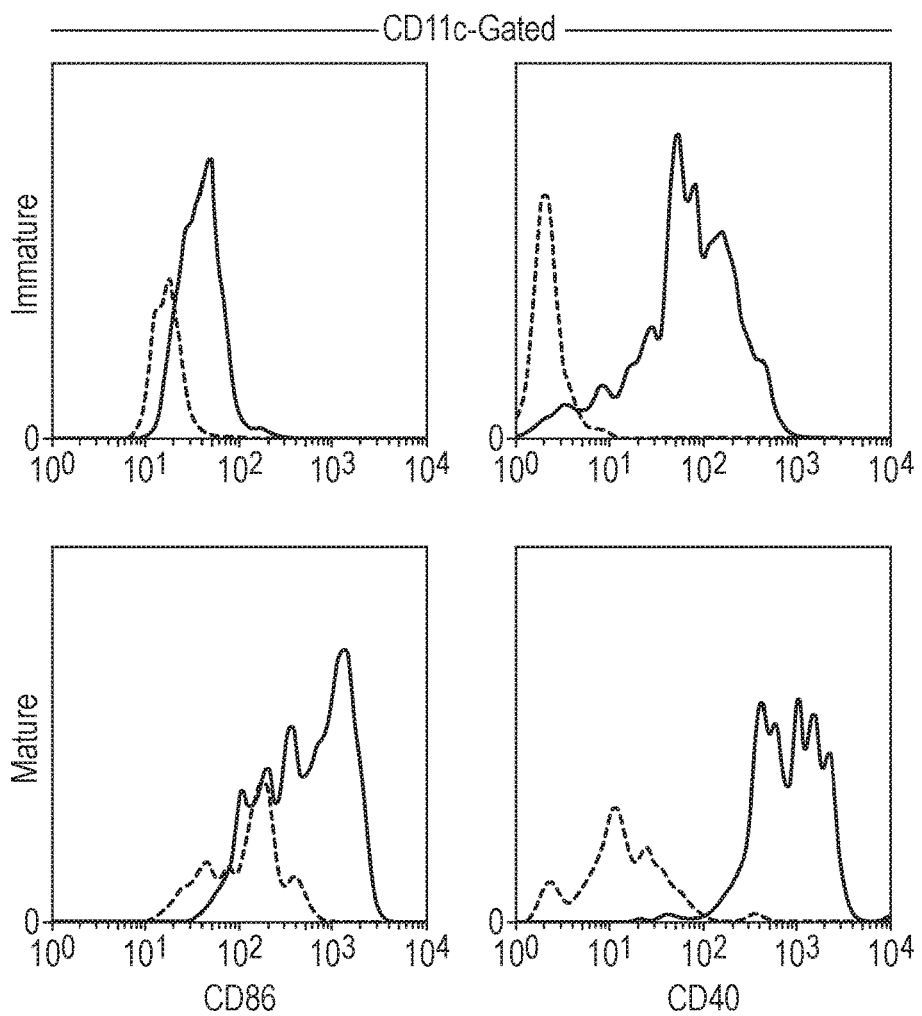

To demonstrate the capacity of human iPSC, derived from terminally-differentiated DC, to re-differentiate along the DC lineage in vitro, iPSC were harvested and permitted to form EBs in vitro using our previously published protocols (Silk K et al. *Gene Therapy* 19: 1035-1040 (2012)). Non-adherent cells liberated from EBs over a 3 week period (FIG. 7A) contained cells highly expressing CD11c (FIG. 7B). Electronic gating of CD11c+ cells revealed an immature DC phenotype, as evidenced by their levels of expression of CD40 and CD86. The capacity of the CD11c+ cells to mature in response to a cocktail of inflammatory cytokines by up-regulating these co-stimulatory molecules was also revealed (FIG. 7C).

The invention claimed is:

1. A method of producing a population of synthetic dendritic cells (DCs), said method comprising:
   culturing induced pluripotent stem cells (iPSCs) produced from a source dendritic cell (DC) under conditions which induce the iPSCs to differentiate into a population of synthetic DCs,
   wherein the synthetic DCs display a definitive adult phenotype comprising the expression of CD11c and MHC class II and the synthetic DCs secrete a greater level of IL-12 than a dendritic cell (DC) displaying a fetal/neonatal phenotype differentiated from an iPSC produced from a somatic cell other than a DC.

2. A method of producing a population of synthetic dendritic cells (DCs) said method comprising:
   (a) producing a population of induced pluripotent stem cells (iPSCs), wherein the iPSCs comprise more than $5 \times 10^5$ iPSCs, and optionally, wherein the population of iPSCs is autologous, allogeneic or semi-allogeneic, and wherein the method of producing the iPSCs comprises:
   (i) culturing source DCs under conditions which reprogram the source DCs to produce the iPSCs, and optionally
   (ii) wherein the method of producing said population of iPSCs comprises culturing the source DCs with a Sendai virus system, a retroviral system comprising reprograming factors, a lentiviral system, messenger RNA, microRNA, small molecules and compounds or other reprogramming factors which is/are capable of reprogramming the source DCs to produce the iPSCs, and optionally
   (iii) wherein the method of producing iPSCs further comprises isolating clonal lines;
   and further optionally, wherein the source DCs are any one of:
   I) a conventional dendritic cell (DC), a plasmacytoid DC, an epidermal Langerhans cell or a dermal DC, optionally wherein the conventional DC is a CD1c+ conventional DC or a CD141+ conventional DC or wherein the plasmacytoid DC is a CD303+ plasmacytoid DC;
   II) ID a DC differentiated from a circulating precursor isolated from peripheral blood, optionally wherein the circulating precursor is a monocyte;
   III) a DC that was modified before it was used to produce an iPSC to (a) increase its immunogenicity or (b) favor a tolerogenic phenotype;
   IV) a human DC; and
   (b) culturing the population of iPSCs produced in step (a) under conditions which induce the iPSCs to differentiate into a population of synthetic dendritic cells DCs, wherein the synthetic DCs display a definitive adult phenotype comprising the expression of CD11c and MHC class II and the synthetic DCs secrete a greater level of IL-12 than a dendritic cell (DC) displaying a fetal/neonatal phenotype differentiated from an iPSC produced from a somatic cell other than a DC.

3. A method of producing a population of synthetic dendritic cells (DCs), said method comprising:
   (a) culturing iPSCs produced from a source dendritic (DC) under conditions which induce the iPSCs to differentiate into synthetic DCs, wherein the source DC is selected from the group consisting of a conventional DC, a plasmacytoid DC, an epidermal Langerhans cells or a dermal DC, wherein the conventional DC is a CD1c+ conventional DC, or a CD141+ conventional DC, wherein:
   (i) the conditions of step a) are Current Good Manufacturing Practice (cGMP) compliant; and/or
   (ii) the method further comprises isolating the population of synthetic DCs re-differentiated from an induced pluripotent stem cell (PSC) produced from a source DC, wherein the synthetic DCs display a definitive adult phenotype comprising the expression of CD11c and MHC class II and the synthetic DCs secrete a greater level of IL-12 than a dendritic cell (DC) displaying a fetal/neonatal phenotype differentiated from an iPSC produced from a somatic cell other than a DC.

4. A method of producing a population of synthetic dendritic cells (DCs), said method comprising:
   (a) producing a population of induced pluripotent stem cells (iPSCs), wherein the iPSCs comprise more than $5 \times 10^5$ iPSCs, and optionally wherein the population of iPSCs is autologous, allogeneic or semi-allogeneic, and wherein the method of producing the population of iPSCs comprises:

(i) culturing source DCs under conditions which reprogram the source DCs to produce the iPSCs, and optionally
(ii) wherein the method of producing said population of iPSCs comprises culturing the source DCs with a Sendai virus system, a retroviral system comprising reprogramming factors, a lentiviral system, messenger RNA, microRNA, small molecules and compounds or other reprogramming factors which is/are capable of reprogramming the source DCs to produce the iPSCs, and optionally
(iii) wherein the method of producing iPSCs further comprises isolating clonal lines;

and further optionally, wherein the source DCs are any one of:
A) a conventional dendritic cell (DC), a plasmacytoid DC, an epidermal Langerhans cell or a dermal DC, optionally wherein the conventional DC is a CD1c+ conventional DC or a CD141+ conventional DC, or wherein the plasmacytoid DC is a CD303+ plasmacytoid DC;
B) a DC differentiated from a circulating precursor isolated from peripheral blood, optionally wherein the circulating precursor is a monocyte;
C) a DC that was modified before it was used to produce an iPSC to (a) increase its immunogenicity or (b) favor a tolerogenic phenotype;
D) a human DC; and (b) culturing the iPSCs produced in step (a) under conditions which induce the iPSCs to differentiate into synthetic DCs wherein the synthetic DCs display a definitive adult phenotype comprising the expression of CD11c and MHC class II and the synthetic DCs secrete a greater level of IL-12 than a dendritic cell (DC) displaying a fetal/neonatal phenotype differentiated from an iPSC produced from a somatic cell other than a DC; and optionally wherein:
(I) the method conditions are Current Good Manufacturing Practice (CGMP) compliant; and/or
(II) the method further comprises isolating the population of synthetic DCs.

* * * * *